United States Patent
Galley et al.

(10) Patent No.: US 7,652,055 B2
(45) Date of Patent: Jan. 26, 2010

(54) 2-IMIDAZOLINES

(75) Inventors: Guido Galley, Rheinfelden (DE);
Katrin Groebke Zbinden, Liestal (CH);
Roger Norcross, Olsberg (CH); Henri Stalder, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/145,541

(22) Filed: Jun. 25, 2008

(65) Prior Publication Data

US 2009/0018180 A1    Jan. 15, 2009

(30) Foreign Application Priority Data

Jul. 2, 2007  (EP) .................. 07111558

(51) Int. Cl.
*A61K 31/4166* (2006.01)
*A61K 31/4168* (2006.01)
*C07D 233/20* (2006.01)
*C07D 233/30* (2006.01)
*C07D 233/42* (2006.01)
*C07D 233/44* (2006.01)

(52) U.S. Cl. ............... 514/398; 548/316.4; 548/326.5; 548/347.1; 514/401

(58) Field of Classification Search .......... 548/316.4, 548/326.5, 347.1; 514/398, 401
See application file for complete search history.

(56) References Cited

U.S. PATENT DOCUMENTS

| | | |
|---|---|---|
| 2,161,938 A | 6/1939 | Sonn |
| 2,457,047 A | 12/1948 | Kyrides |
| 2,731,471 A | 1/1956 | Synerholm et al. |
| 2,744,909 A | 5/1956 | Speeter |
| 2,744,910 A | 5/1956 | Speeter |
| 2,778,836 A | 1/1957 | Morren |
| 2,919,274 A | 12/1959 | Faust et al. |
| 3,161,653 A | 12/1964 | Fruhstorfer et al. |
| 3,354,175 A | 11/1967 | Fruhstorfer et al. |
| 3,377,247 A | 4/1968 | Elbe |
| 3,480,630 A | 11/1969 | Stahle et al. |
| 3,483,203 A | 12/1969 | Werner |
| 3,586,695 A | 6/1971 | Wysong et al. |
| 3,622,579 A | 11/1971 | Stahle et al. |
| 3,660,423 A | 5/1972 | Wysong et al. |
| 3,758,476 A | 9/1973 | Rippel et al. |
| 3,818,035 A | 6/1974 | Binon et al. |
| 3,818,094 A | 6/1974 | Stahle et al. |
| 3,992,403 A | 11/1976 | Roebke |
| 4,125,620 A | 11/1978 | Stahle et al. |
| 4,146,647 A | 3/1979 | Lafon |
| 4,254,133 A | 3/1981 | Kristinsson et al. |
| 4,323,570 A | 4/1982 | Stenzel et al. |
| 4,443,464 A | 4/1984 | Biedermann et al. |
| 4,665,095 A | 5/1987 | Winn et al. |
| 5,610,174 A | 3/1997 | Craig et al. |
| 5,658,938 A | 8/1997 | Geerts et al. |
| 2002/0019390 A1 | 2/2002 | Wong et al. |
| 2003/0181354 A1 | 9/2003 | Abdulrazik |
| 2003/0236274 A1 | 12/2003 | Tasaka et al. |

FOREIGN PATENT DOCUMENTS

| | | |
|---|---|---|
| CA | 2246027 | 2/2000 |
| DE | 1935479 | 1/1971 |
| DE | 1695005 | 2/1971 |
| DE | 2750902 | * 5/1978 |
| DE | 2818367 | 11/1978 |
| DE | 3133887 | 3/1983 |
| EP | 0 024 829 | 3/1981 |
| EP | 0086043 | 8/1983 |
| EP | 0 125 410 | 11/1984 |
| EP | 0 166 937 | 1/1986 |
| EP | 0 331 374 | 9/1989 |
| EP | 0 424 059 | 4/1991 |
| EP | 0 857 483 | 8/1998 |
| EP | 0 924 209 | 6/1999 |

(Continued)

OTHER PUBLICATIONS

Areschka, A et al, *Chimie Therapeutiquei*, 7(4) 337-344 (1972).

(Continued)

*Primary Examiner*—Kamal A Saeed
*Assistant Examiner*—Janet L Coppins
(74) *Attorney, Agent, or Firm*—George W. Johnston; Patricia S. Rocha-Tramaloni; Kimberly J. Prior

(57) ABSTRACT

The present invention relates to compounds of formula I

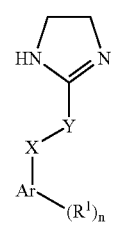

I wherein
X—Y, $R^1$, and n are as defined herein and to their pharmaceutically active salts. Compounds of formula I have a good affinity to the trace amine associated receptors (TAARs), especially for TAAR1 and are useful for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

20 Claims, No Drawings

FOREIGN PATENT DOCUMENTS

| | | |
|---|---|---|
| EP | 1 103 243 | 5/2001 |
| EP | 1 413 576 | 4/2004 |
| ES | 323 985 | 12/1966 |
| FR | 6 551 | 12/1968 |
| GB | 877306 | 9/1961 |
| GB | 1016514 | 1/1966 |
| GB | 1181356 | * 2/1970 |
| WO | WO 96/22768 | 8/1996 |
| WO | WO 97/12874 | 4/1997 |
| WO | WO 98/12183 | 3/1998 |
| WO | WO 00/66563 | 11/2000 |
| WO | WO 01/30762 | 5/2001 |
| WO | WO 01/81334 | 11/2001 |
| WO | WO 02/22801 | 3/2002 |
| WO | WO 02/40453 | 5/2002 |
| WO | WO 02/076950 | 10/2002 |
| WO | WO 03/0092374 | 11/2003 |
| WO | WO 2004/014898 | 2/2004 |
| WO | WO 2006/107923 | 10/2006 |
| WO | WO 2006/119411 | 11/2006 |
| WO | WO 2007/024944 | 3/2007 |
| WO | WO 2008/123821 | 10/2008 |

OTHER PUBLICATIONS

Deutch et al., (1999) Neurotransmitters. In Fundamental Neuroscience (2$^{nd}$ ed.) pp. 193-234, Academic Press.
Wong, et al., (2001) Nat. Rev. Neurosci. 2, pp. 343-351.
Carlsson. et al. (2001) Annu Rev. Pharmacol. Toxicol. 41, pp. 237-260.
Tuite et al., (2003) Expert Opin. Investig. Drugs 12, pgs. 1335-1352.
Castellanos et al., (2002) Nat. Rev. Neurosci. 3, pp. 617-628.
Usdin, E.; Sandler, M.; Editors. Psychopharmacology Series, vol. 1: Trace Amines and the Brain. [Proceedings of a Study Group at the 14th Annual Meeting of the American College of Neuropsychoparmacology, San Juan, Puerto Rico](1976), pp. 1-281.
Lindemann et al., (2005) Trends in Pharmacol. Sci. 26, pp. 274-281.
Branchek et al., (2003) Curr. Opin. Pharmacol. 3, pp. 90-97.
Premont et al. (2001) Proc. Natl. Acad. Sci. U. S. A. 98, pp. 9474-9475.
Mousseau et al., (1995) Prog. Brain Res. 106, pp. 285-291.
McCormack et al. (1986) J. Neurosci. 6, pp. 94-101.
Dyck, L. E. (1989) Life Sci. 44, pp. 1149-1156.
Parker, et al. (1988) J. Pharmacol. Exp. Ther. 245, pp. 199-210.
Lindemann et al. (2005) Genomics 85, pp. 372-385.
Moormann, et al., (1990) J. Med. Chem. pp. 614-626.
Hlasta et al., (1987) vol. 30, J. Med. Chem. pp. 1555-1562.
Dash et al., (2006) J. Heterocyclic Chem. pp. 401-404.
Gentili et al., (2004) J. Med. Chem. vol. 47 pp. 6160-6173.
Dias et al. (2005) J. Med. Chem. Vol. 40 pgs. 1206-1213.
Pigini et al., (1987) Eur. J. Med. Chem. vol. 22 pp. 273-276.
Wu et al., Synthesis (2003) pp. 1657-1660.
Fujioka et al., (2005) Tetrahedron Lett. vol. 46, pp. 2197-2199.
Ishihara et al., Synlett (2006) pp. 227-230.
Pinza et al. (1976) Heterocycles. vol. 4 pp. 1699-1706.
Kornicka et al. (2006) Heterocycles vol. 68 pp. 687-699.
Kosasayama et al., (1979) Chem. Pharm. Bull. vol. 27 pp. 831-840.
Lloyd et al., (1980) Tetrahedron vol. 36, pp. 2675-2679.
Flippin et al., Tetrahedron Letters, vol. 34, pp. 3255-3258 (1993).
Liebigs, Ann. Chem. pp. 2061-2071 (1980).
Huh et al., Tetrahedron, vol. 58, pp. 9925-9932 (2002).
Huh et al., Tetrahedron, vol. 60, pp. 9857-9862 (2004).
Law et al., J. Med. Chem. vol. 41, pp. 2243-2251 (1998).
Debernardis et al., J. Med. Chem. vol. 29, pp. 1413-1417 (1986).
Mohammadpoor-Baltork, Bull. Korean Chem. Soc. vol. 24, p. 1354-1356 (2003).
Abdollahi-Alibeik et al., Bioorg. Med. Chem. Lett. vol. 14, pp. 6079-6082 (2004).
Amemiya, Synth. Commun. vol. 20, pp. 2483-2489 (1990).
Ohta, Chem. Pharm. Bull. vol. 35, pp. 1058-1069 (1987).
Olah, Synlett pp. 647-650 (1992).
Katz et al., Tetrahedron, vol. 45, pp. 1801-1814 (1989).
Wentland et al., J. Med. Chem. vol. 30, pp. 1482-1489 (1987).
Campos et al., Heterocycles, vol. 40, p. 841-849 (1995).
Ohta, Synthesis, pp. 78-81 (1990).
Mancuso et al., J. Org. Chem. vol. 43, pp. 2480-2482 (1978).
Mohammadpoor-Baltork, Synlett, pp. 2803-2805 (2004).
Cahiez et al., Synthesis, pp. 2138-2144 (1999).
Evans et al., Tetrahedron Lett. vol. 39, pp. 2937-2940 (1998).
Nakamura et al., J. Chem. Soc. Perkin Trans. 1, pp. 1061-1066 (2002).
Turner, et al. (1991) J. Org. Chem. vol. 56, pp. 5739-5740.
Zhang et al., J. Med. Chem. 1997, 40, pp. 3014-3024.
Khimiya Geterotsiklicheskikh Soedinenii, 1988, pp. 77-79.
Reimann et al., Arch. Pharm. 1989, vol. 322, pp. 363-367.
Klapars, et al., J. Am. Chem. Soc. 2001, vol. 123, pp. 7727-7729.
Anderson, et al., Tetrahedron, 2002, vol. 58, pp. 8475-8481.
Touzeau et al., J. Med. Chem. 2003, vol. 46, pp. 1962-1979.
Altenbach et al., Synthesis and Structure-Activity Studies on N-[5-(1H-Imidazol-4-yl)-5,6,7,8-tetrahydro-1-naphthalenyl]methanesulfonamide, an Imidasole-Containing $\alpha_{1A}$-Adrenoceptor Agonist, J. Med. Chem. (2004), 47: 3220-3235.
Amemiya et al., Synthesis and $\alpha$-Adrenergic Activities of 2-and 4-Substituted Imidazoline and Imidazoline Analogues, J. Med. Chem. (1992), 35:750-755.
Bagley et al., Synthesis and $\alpha_2$-Adrenergic Activities of Imidazole and Imidazolidine Analogues: In Vitro and In Vivo Selectivity, Medicinal Chemistry Research (1994), 4:346-364.
Branchek et al., Trace amine receptors as targets for novel therapeutics: legend, myth and fact, Curr. Opin. Phamacol. (2003), 3:90-97.
Bunzow et al., Amphetamine, 3,4-Methylenedioxymethamphetamine, Lysergic Acid Diethylamide, and Metabolites of the catecholamine Neurotransmitters Are Agonists of a Rat Trace Amine Receptor, Molecular Pharmacology (2001), 60: 1181-1188.
Carroll et al., In Vitro and In Vivo Characterization of Alpha-1A Selective Agonists and Their Utility for Stress Incontinence, Med. Chem. Res. (2004), 13:134-148.
De Bernardis et al., Conformationally Defined Adregernic Agents. 5. Resolution, Absolute Configuration, and Pharmacological Characterization of the Enantiomers of 2-(5,6-Dihydroxy-1,2,3,4-tetrahydro-1-naphthyl)imidazoline: A Potent Agonist at $\alpha$-Adrenoceptors, J. Med. Chem. (1987), 30:1011-1017.
Faust et al., Antihypertensive Agents: Derivatives of 2-Imidazoline and 1,4,5,6-Tetrahydropyrimidine, J. Org. Chem. (1961), 26: 4044-4047.
Hirashima et al., Three-Dimensional Common-Feature Hypotheses for Octopamine Agonist 2-(Arylimino)imidazolidines, Bioorganic & Medicinal Chemistry (2002), 10:117-123.
Holt, A., Imidazoline binding sites on receptors and enzymes:Emerging targets for novel antidepressant drugs?, Journal of Psychiatry & Neuroscience (2003), 28:409-414.
Jetter et al., Synthesis of 4-Substituted Imidazoles via Palladium-Catalyzed Cross-Coupling Reactions, Synthesis (1998), 829-831.
Law et al., Benzylimidazolines as h5-HT$_{1B/1D}$ Serotonin Receptor Ligands: A Structure-Affinity Investigation, J. Med. Chem. (1998), 41:2243-2251.
Lee et al., 4-[(N-Imidazol-2-ylmethyl)aniline]pyranopyridine Analogs as Novel Anti-Angiogenic Agents, Bull. Korean Chem. Soc. (2005), 25: 619-628.
Matsunaga et al., C$_{17,20}$ inhibitors. Part 2: Design, synthesis and structure-activity relationships of (2-naphthylmethyl)-1H-imidazoles as novel C$_{17,20}$-lyase inhibitors, Bioorganic & Medicinal Chemistry (2004), 4314.
Matsunaga et al., Synthetic studies on (1$_S$)-6,7-dimethoxy-2-naphthyl)-1-(1H-imidazol-4-yl)2-methylpropan-l-ol as a selective C$_{17,20}$-lyase inhibitor, Tetrahedron: Asymmetry (2004), 15: 2021-2028.
Mclennan, P;L., The Hypothermic Effect of Clonidine and Other Imidazolidines in Relation to their Ability to Enter the Central Nervous System in Mice, European Journal of Pharmacology (1981), 69:477-482.

Nathanson, J.A.,Phenyliminoimidazolines: Characterization of a Class of Potent Agonists of Octopamine-Sensitive Adenylate Cylcase and Their Use in Understanding the Pharmacology of Octopamine Receptors, Amer. Soc. Pharmacology (1985), 28:254-268.

Ojida et al., Sterocontrolled synthesis of (1S)-1-(1H-imidazol-4-yl)-1-(6-methoxy-2-napthyl)-2-methylpropan-1-ol as a potent $C_{17,20}$-lyase inhibitor,Tetrahedron: Asymmetry (2004), 15: 1555-1559.

Olmos et al., Imidazolines stimulate release of insulin from RIN-5AH cells independently from imidazoline $I_1$ and $I_2$ receptors, European Journal of Pharmacology (1994), 262: 41-48.

Prisinzano et al., 2-(aniline)imidazolines and 2-(benzyl)imidazoline derivatives as $h5$ -HT-$_{1D}$ serotonin receptor ligands, Bioorganic & Medicinal Chemistry Letter (2004), 14:4697-4699.

Savola et al., Cardiovascular and Sedative α-Adrenoceptor Effects of Detomidine-like Arylalkyl Imidazoles and Associated Derivatives, Drug Res. (1988), 38:29-35.

Timmermans et al., Characterization of α-Adrenoceptor Populations. Quantitive Relationships between Cardiovascular Effects Initiated at Central and Peripheral α-Adrenoceptors, J. Med. Chem. (1981), 24:502-507.

Timmermans et al., Correlations between Central Hypotensive and Peripheral Hypertensive Effects of Structurally Dissimilar Alpha-Adrenoceptor Agonists, Life Sciences (1981), 28:653-660.

Turner et al., A Facile Route to Imidazol-4-yl Anions and Their Reaction with Carbonyl Compounds, J. Org. Chem. (1991), 56: 5739-5740.

Freiter, E.R., et al., J. Heterocyclic Chem., vol. 10, No. 3, pp. 391-394 (1973), XP008087527.

Tarnchompoo, B., et al., vol. 31, No. 40, pp. 5779-5780 (1990), XP002118267.

Wilkinson, C.F., et al., Biochem. Pharmacol., vol. 21, pp. 3187- 3192 (1972), XP :008087536.

Raddatz, Rita , et al., J. Pharmacol. Exp. Therap., vol. 292, No. 3, pp. 1135-1145 (2000), XP008087488.

Shafiee, A., et al., Journal of Heterocyclic Chemistry, pp. 607-610 (1998), XP001069546.

Robertson, David W., J. Med. Chem., vol. 29, pp. 1577-1586 (1986), XP008087539.

Database CA, Chemical Abstracts, Yamaguchi, Hideaki, XP002465006 & JP 06 268356 (1994).

* cited by examiner

2-IMIDAZOLINES

PRIORITY TO RELATED APPLICATION(S)

This application claims the benefit of European Patent Application No. 07111558.8, filed Jul. 2, 2007, which is hereby incorporated by reference in its entirety.

BACKGROUND OF THE INVENTION

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlap with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9]. For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "cross reacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors.

REFERENCES USED

1 Deutch, A. Y. and Roth, R. H. (1999) Neurotransmitters. In *Fundamental Neuroscience* (2$^{nd}$ edn) (Zigmond, M. J., Bloom, F. E., Landis, S. C., Roberts, J. L, and Squire, L. R., eds.), pp. 193-234, Academic Press;
2 Wong, M. L. and Licinio, J. (2001) Research and treatment approaches to depression. *Nat. Rev. Neurosci.* 2, 343-351;
3 Carlsson, A. et al. (2001) Interactions between monoamines, glutamate, and GABA in schizophrenia: new evidence. *Annu. Rev. Pharmacol. Toxicol.* 41, 237-260;
4 Tuite, P. and Riss, J. (2003) Recent developments in the pharmacological treatment of Parkinson's disease. *Expert Opin. Investig. Drugs* 12, 1335-1352,
5 Castellanos, F. X. and Tannock, R. (2002) Neuroscience of attention-deficit/hyperactivity disorder: the search for endophenotypes. *Nat. Rev. Neurosci.* 3, 617-628;
6 Usdin, Earl; Sandler, Merton; Editors. *Psychopharmacology Series, Vol.* 1: *Trace Amines and the Brain*. [Proceedings of a Study Group at the 14*th Annual Meeting of the American College of Neuropsychopharmacology*, San Juan, Puerto Rico] (1976);
7 Lindemann, L. and Hoener, M. (2005) A renaissance in trace amines inspired by a novel GPCR family. *Trends in Pharmacol. Sci.* 26, 274-281;
8 Branchek, T. A. and Blackburn, T. P. (2003) Trace amine receptors as targets for novel therapeutics: legend, myth and fact. *Curr. Opin. Pharmacol.* 3, 90-97;
9 Premont, R. T. et al. (2001) Following the trace of elusive amines. *Proc. Natl. Acad. Sci. U.S.A.* 98, 9474-9475;
10 Mousseau, D. D. and Butterworth, R. F. (1995) A high-affinity [3H] tryptamine binding site in human brain. *Prog. Brain Res.* 106, 285-291;
11 McCormack, J. K. et al. (1986) Autoradiographic localization of tryptamine binding sites in the rat and dog central nervous system. *J. Neurosci.* 6, 94-101;
12 Dyck, L. E. (1989) Release of some endogenous trace amines from rat striatal slices in the presence and absence of a monoamine oxidase inhibitor. *Life Sci.* 44, 1149-1156;
13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;
14 Lindemann, L. et al. (2005) Trace amine associated receptors form structurally and functionally distinct subfamilies of novel G protein-coupled receptors. *Genomics* 85, 372-385.

SUMMARY OF THE INVENTION

The present invention provides compounds of formula I

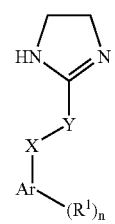

wherein
X—Y is —N($R^2$)—CH($R^3$)—, CH($R^3$)—N($R^2$)—, —NH—NH—, —O—CH$R^3$—, —CH$R^3$—O—, —S—CH$R^3$, —CH$R^3$—S— or —CH$R^3$—CH$R^3$—,
$R^1$ is hydrogen,
  halogen,
  lower alkyl,
  lower alkoxy,
  —(CH$_2$)$_o$-phenyl optionally substituted by lower alkoxy,
  —(CH$_2$)$_o$—C(O)-phenyl optionally substituted by lower alkoxy, —(CH$_2$)$_o$—O-phenyl optionally substituted by lower alkoxy,
—(CH$_2$)$_o$—O-phenyl,
CF$_3$,
cycloalkyl,
NO$_2$,
amino or
hydroxy;
R$^2$ is hydrogen,
lower alkyl,
phenyl optionally substituted by hydroxy or benzyl;
R$^3$ and R$^{3'}$ are each independently
hydrogen,
lower alkyl or
benzyl;
Ar is phenyl,
naphthyl,
benzofuranyl or
benzo[1,3]dioxolyl;
n is 1, 2, 3 or 4; and
o is 0, 1, 2, 3 and their pharmaceutically active salts, with the exception of the following compounds:
(4-chloro-phenyl)-(4,5-dihydro-1H-imidazol-2-ylmethyl)-amine (CAS 67083-84-5);
(3-chloro-phenyl)-(4,5-dihydro-1H-imidazol-2-ylmethyl)-amine (CAS 745732-75-6); (4,5-dihydro-1H-imidazol-2-ylmethyl)-ethyl-phenyl-amine (CAS 37411-36-2);
3-[(4,5-dihydro-1H-imidazol-2-ylmethyl)-p-tolyl-amino]-phenol (CAS 50-60-2);
benzyl-(4,5-dihydro-1H-imidazol-2-ylmethyl)-phenyl-amine (CAS 91-75-8);
2-(4-benzyl-phenoxymethyl)-4,5-dihydro-1H-imidazole (CAS 213400-55-6);
2-(4-phenethyl-phenoxymethyl)-4,5-dihydro-1H-imidazole (CAS 109814-01-9);
2-(2,3,6-trimethyl-phenoxymethyl)-4,5-dihydro-1H-imidazole (CAS 68959-93-3);
2-(2,6-dichloro-phenoxymethyl)-4,5-dihydro-1H-imidazole (CAS 21244-83-7);
2-(2-chloro-phenoxymethyl)-4,5-dihydro-1H-imidazole (65248-69-3);
2-(biphenyl-2-yloxymethyl)-4,5-dihydro-1H-imidazole (CAS 193070-40-5);
2-(2,3-dichloro-phenoxymethyl)-4,5-dihydro-1H-imidazole (CAS 68959-95-5);
2-(biphenyl-4-yloxymethyl)-4,5-dihydro-1H-imidazole (CAS 858222-61-4);
2-(2-methoxy-phenoxymethyl)-4,5-dihydro-1H-imidazole (CAS 762188-54-5);
2-(naphthalen-2-yloxymethyl)-4,5-dihydro-1H-imidazole (CAS 107774-80-1);
2-(4-chloro-phenoxymethyl)-4,5-dihydro-1H-imidazole (CAS 103038-98-8);
2-(3-trifluoromethyl-phenoxymethyl)-4,5-dihydro-1H-imidazole (CAS 72422-05-0);
2-(2,4-dichloro-phenoxymethyl)-4,5-dihydro-1H-imidazole (CAS 68959-96-6);
2-[1-(2-benzyloxy-phenoxy)-2-phenyl-ethyl]-4,5-dihydro-1H-imidazole (CAS 150016-78-7);
2-(2-cyclopropyl-phenoxymethyl)-4,5-dihydro-1H-imidazole (CAS 40600-13-3);
2-[1-(2,6-dichloro-phenoxy)-ethyl]-4,5-dihydro-1H-imidazole (CAS 31036-80-3);
2-(3-chloro-phenoxymethyl)-4,5-dihydro-1H-imidazole (CAS 103040-25-1);
2-phenoxymethyl-4,5-dihydro-1H-imidazole (CAS 65248-68-2);
2-phenethyl-4,5-dihydro-1H-imidazole (CAS 26038-62-0);
N-(3-chloro-2-methyl-phenyl)-N'-(4,5-dihydro-1H-imidazol-2-yl)-hydrazine (CAS 46425-56-3);
benzyl-(4,5-dihydro-1H-imidazol-2-yl)-amine (CAS 6182-2-1);
2-(3,4-dichloro-phenylsulfanylmethyl)-4,5-dihydro-1H-imidazole (CAS 113698-37-6);
2-(2,4-dichloro-benzylsulfanyl)-4,5-dihydro-1H-imidazole (CAS 938156-72-0);
2-(3-chloro-4-propoxy-benzylsulfanyl)-4,5-dihydro-1H-imidazole (CAS 63549-90-6);
2-(3-nitro-4-propoxy-benzylsulfanyl)-4,5-dihydro-1H-imidazole (CAS 325983-20-8);
2-benzylsulfanyl-4,5-dihydro-1H-imidazole (CAS 5455-64-1);
2-(2-chloro-6-fluoro-benzylsulfanyl)-4,5-dihydro-1H-imidazole (CAS 913689-07-3);
2-(3-chloro-4-ethoxy-benzylsulfanyl)-4,5-dihydro-1H-imidazole (CAS 325983-19-5);
2-(2,6-dichloro-benzylsulfanyl)-4,5-dihydro-1H-imidazole (CAS 64204-41-7); and
2-(3,4-dichloro-benzylsulfanyl)-4,5-dihydro-1H-imidazole (CAS 86366-97-4).

The specific compounds excluded from the scope of new compounds of formula I are described for example in the below mentioned references or are enclosed in public chemical libraries.

The invention includes all racemic mixtures, all their corresponding enantiomers and/or optical isomers.

In addition, all tautomeric forms of compounds of formula I are also encompassed by the present invention.

The invention also provides pharmaceutical compositions containing a therapeutically effective amount of a compound of formula I or a pharmaceutically active salt thereof. The invention further provides methods for the manufacture of the compounds and compositions of the invention.

Compounds of formula I have a good affinity to the trace amine associated receptors (TAARs), especially for TAAR1.

The compounds are useful for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety and attention deficit hyperactivity disorder (ADHD).

DETAILED DESCRIPTION OF THE INVENTION

The following definitions of general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group having a lower alkyl residue as defined above that is attached via an oxygen atom.

The term "halogen" denotes chlorine, iodine, fluorine and bromine.

The term "cycloalkyl" denotes a saturated carboxylic ring containing from 3 to 6 carbon atoms.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

Preferred compounds of formula I are those, wherein Ar is phenyl.

Especially preferred are compounds from this group, wherein X—Y is —N($R^2$)—CH($R^3$)—, for example the following compounds (4-chloro-phenyl)-(4,5-dihydro-1H-imidazol-2-ylmethyl)-amine, (3-chloro-phenyl)-(4,5-dihydro-1H-imidazol-2-ylmethyl)-amine, (4-bromo-3-chloro-phenyl)-(4,5-dihydro-1H-imidazol-2-ylmethyl)-amine, (4-chloro-3-fluoro-phenyl)-(4,5-dihydro-1H-imidazol-2-ylmethyl)-amine, (3-chloro-phenyl)-(4,5-dihydro-1H-imidazol-2-ylmethyl)-methyl-amine, (3,4-dichloro-phenyl)-(4,5-dihydro-1H-imidazol-2-ylmethyl)-methyl-amine, (4,5-dihydro-1H-imidazol-2-ylmethyl)-[4-(4-methoxy-benzyl)-phenyl]-amine and (4,5-dihydro-1H-imidazol-2-ylmethyl)-(2-methoxy-phenyl)-methyl-amine.

Further preferred are compounds, wherein X—Y is —O—CHR$^3$—, such as 2-(2-chloro-phenoxymethyl)-4,5-dihydro-1H-imidazole, 2-(2,3-dichloro-phenoxymethyl)-4,5-dihydro-1H-imidazole, 2-(3-trifluoromethyl-phenoxymethyl)-4,5-dihydro-1H-imidazole, 2-[1-(2,6-dichloro-phenoxy)-ethyl]-4,5-dihydro-1H-imidazole, 3-{4-[1-(4,5-dihydro-1H-imidazol-2-yl)-ethoxy]-phenyl}-1-(4-isopropoxy-phenyl)-propan-1-one, 2-[4-(4-isopropoxy-phenoxymethyl)-phenoxymethyl]-4,5-dihydro-1H-imidazole, 2-(3-benzyl-phenoxymethyl)-4,5-dihydro-1H-imidazole, 2-[4-(3-phenyl-propyl)-phenoxymethyl]-4,5-dihydro-1H-imidazole, 2-(2-chloro-3-trifluoromethyl-phenoxymethyl)-4,5-dihydro-1H-imidazole, 2-(2,3-difluoro-phenoxymethyl)-4,5-dihydro-1H-imidazole, 4-(4,5-dihydro-1H-imidazol-2-ylmethoxy)-2,3-dimethyl-phenol and 2-(3,4-dichloro-phenoxymethyl)-4,5-dihydro-1H-imidazole.

Preferred are further compounds, wherein X—Y is —NH—NH—, for example

N-(3-chloro-2-methyl-phenyl)-N'-(4,5-dihydro-1H-imidazol-2-yl)-hydrazine and

N-(4,5-dihydro-1H-imidazol-2-yl)-N'-(3,4-dimethyl-phenyl)-hydrazine.

A further preferred group for Ar is phenyl are compounds, wherein X—Y is —S—CHR$^3$—, for example 2-(2,3-dichloro-phenylsulfanylmethyl)-4,5-dihydro-1H-imidazole.

Preferred compounds of formula I are further those, wherein Ar is benzofuranyl and X—Y is —N($R^2$)—CHR$^3$— or —O—CHR$^3$, for example (4,5-dihydro-1H-imidazol-2-ylmethyl)-(4-methyl-benzofuran-5-yl)-amine and 2-(benzofuran-6-yloxymethyl)-4,5-dihydro-1H-imidazole.

The present compounds of formula I and their pharmaceutically acceptable salts can be prepared by methods known in the art, for example, by processes described below, which process comprises a) reacting an ester of formula

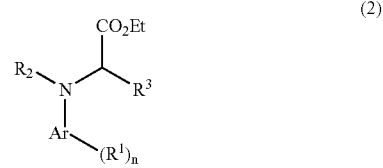

with an in sito prepared product from ethylenediamine with trimethylaluminium to give a compound of formula

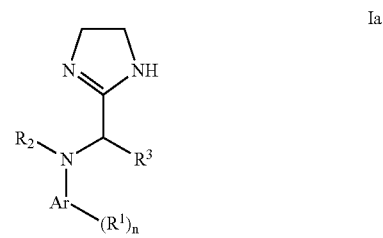

wherein the substituents are as defined above, or b) reacting a nitrile derivative of formula

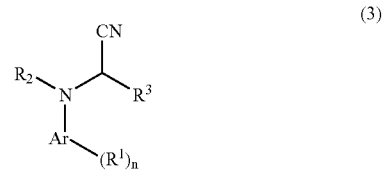

with ethylendiamine in the presence of thioacetamide to give a compound of formula

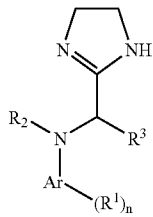
(Ia)

wherein the substituents are as defined above, or c) reacting an ester derivative of formula

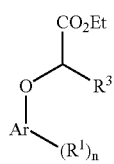
(7)

with an in sito prepared product from ethylenediamine with trimethylaluminium to give a compound of formula

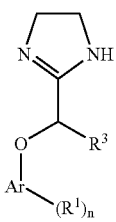
(Ib)

wherein the substituents are as defined above, or d) reacting an ester derivative of formula

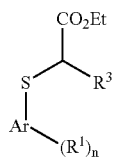
(9)

with an in sito prepared product from ethylenediamine with trimethylaluminium to give a compound of formula

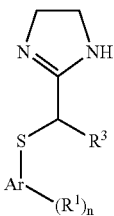
(Ic)

wherein the substituents are as defined above, or e) reacting an ester derivative of formula

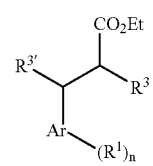
(13)

with an in sito prepared product from ethylenediamine with trimethylaluminium to give a compound of formula

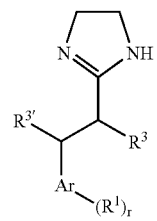
(Id)

wherein the substituents are as defined above, or f) reacting a compound of formula

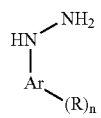
(14)

with a compound of formula (15)

to give a compound of formula

[Chemical structure: 2-amino-imidazoline with NH-Ar(R¹)ₙ substituent via HN-NH linker]

wherein the substituents are as defined above, or g) reacting a compound of formula

[Chemical structure (16): R³-CH(Ar(R¹)ₙ)-NH-R²]

with a compound of formula

[Chemical structure (15): 2-(methylthio)-imidazoline]

to give a compound of formula

[Chemical structure If: imidazoline-N(R²)-CH(R³)-Ar(R¹)ₙ]

wherein the substituents are as defined above, or h) reacting a compound of formula

[Chemical structure (17): R³-CH(Br)-Ar(R¹)ₙ]

with a compound of formula

[Chemical structure (18): 2-thioxo-imidazolidine]

to give a compound of formula

[Chemical structure Ig: imidazoline-S-CH(R³)-Ar(R¹)ₙ]

wherein the substituents are as defined above, and if desired, converting the compounds obtained into pharmaceutically acceptable acid addition salts.

The compounds of formula I can be prepared in accordance with the process variants a) to h) as described above and with the following schemes 1-7. The starting materials are either commercially available, are otherwise known in the chemical literature, or can be prepared in accordance with methods well known in the art.

Scheme 1 (Method 1)

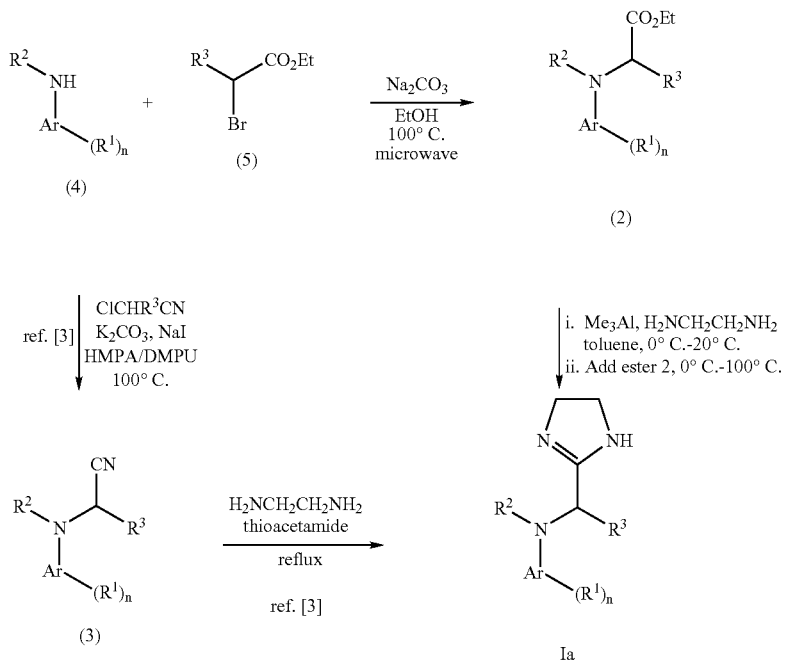

Compounds of formula I in which —X—Y— is —N(R²)—CH(R³)— can be prepared by the route shown in Scheme 1. In the first step an aniline derivative of formula (4) is reacted with an alpha-bromo-ester compound of formula (5) in the presence of a base such as sodium carbonate. The reaction is carried out in an alcoholic solvent such as ethanol, at elevated temperature, preferably at around 100° C. in a closed vessel under microwave irradiation. Alternative reagents to accomplish this transformation have been reported in reference [1]. The resulting product, an ester derivative of formula (2), is then reacted with a reagent which is first prepared in situ by treating ethylenediamine with trimethylaluminium at a temperature between 0° C. and room temperature in an inert organic solvent such as toluene, following a procedure reported in references [1] & [2]. The reaction between ester (2) and the aluminium-dialkylamine reagent is performed in an inert solvent such as toluene at an elevated temperature such as the reflux temperature of the solvent.

[1] Moormann, A. E. et al. *J. Med. Chem.* 1990, 33, 614-626.
[2] Hlasta, D. J. et al. *J. Med. Chem.* 1987, 30, 1555-1562.

Alternatively, compounds of formula I in which —X—Y— is —N(R²)—CH(R³)— can be prepared by using the procedures described in reference [3], in which the aniline derivative of formula (4) is first reacted with a corresponding chloroacetonitrile to afford a nitrile derivative of formula (3) which is subsequently reacted with ethylenediamine in the presence of thioacetamide to afford the compounds of formula Ia.

[3] Dash, P.; Kudav, D. P.; Parihar J. A. *J. Heterocyclic Chem.* 2006, 43, 401-404.

Scheme 2 (Method 2)

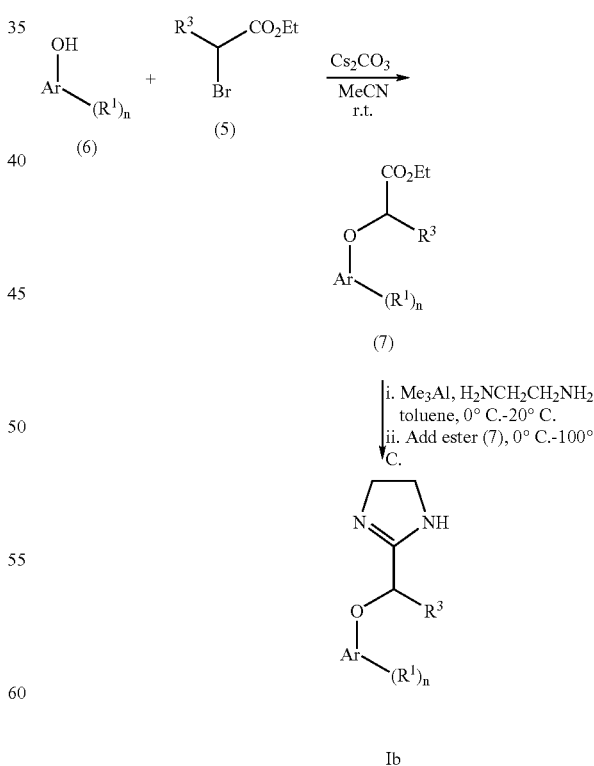

Compounds of formula I in which —X—Y— is —O—CH (R³)— can be prepared by the route shown in Scheme 2. In the first step a phenol derivative of formula (6) is reacted with an alpha-bromo-ester compound of formula (5) in the presence of a base such as cesium carbonate. The reaction is carried out in a polar organic solvent such as acteonitrile, preferably at room temperature. Alternative reagents to accomplish this transformation have been reported in reference [1]. The resulting product, an ester derivative of formula (7), is then reacted with a reagent which is first prepared in situ by treating ethylenediamine with trimethylaluminium at a temperature between 0° C. and room temperature in an inert organic solvent such as toluene, following a procedure reported in references [1]-[4]. The reaction between ester (7) and the aluminium-diakylamine reagent is performed in an inert solvent such as toluene at an elevated temperature such as the reflux temperature of the solvent.

[1] Moormann, A. E. et al. *J. Med. Chem.* 1990, 33, 614-626.
[2] Hlasta, D. J. et al. *J. Med. Chem.* 1987, 30, 1555-1562.
[4] Gentili, F. et al. *J. Med. Chem.* 2004, 47, 6160-6173.

Alternatively, compounds of formula I in which —X—Y— is —O—CH($R^3$)— can be prepared by methods described in the following reference [5].

[5] Dias, N. et al. *Eur. J. Med. Chem.* 2005, 40, 1206-1213.

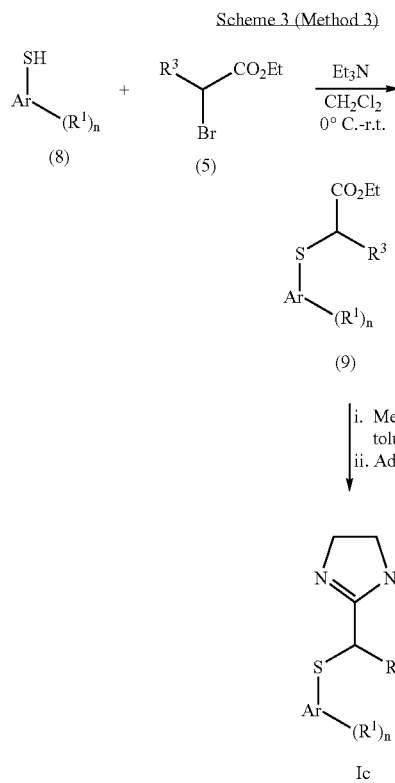

Compounds of formula I in which —X—Y— is —S—CH($R^3$)— can be prepared by the route shown in Scheme 3. In the first step a thiophenol derivative of formula (8) is reacted with an alpha-bromo-ester compound of formula (5) in the presence of a base such as triethylamine. The reaction is carried out in an inert organic solvent such as dichloromethane, preferably at a temperature between 0° C. and room temperature. Alternative reagents to accomplish this transformation have been reported in reference [1]. The resulting product, an ester derivative of formula (9), is then reacted with a reagent which is first prepared in situ by treating ethylenediamine with trimethylaluminium at a temperature between 0° C. and room temperature in an inert organic solvent such as toluene, following a procedure reported in references [1] & [2]. The reaction between ester (9) and the aluminium-diakylamine reagent is performed in an inert solvent such as toluene at an elevated temperature such as the reflux temperature of the solvent.

[1] Moormann, A. E. et al. *J. Med. Chem.* 1990, 33, 614-626.
[2] Hlasta, D. J. et al. *J. Med. Chem.* 1987, 30, 1555-1562.

Alternatively, compounds of formula I in which —X—Y— is —S—CH($R^3$)— can be prepared by methods described in the following reference [6].

[6] Pigini, M. et al. *Eur. J. Med. Chem.* 1987, 22, 273-276.

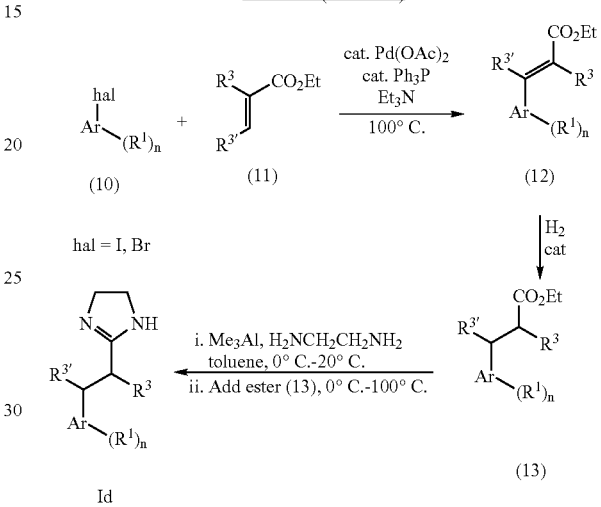

Compounds of formula I in which —X—Y— is —CH($R^{3'}$)—CH($R^3$)— can be prepared by the route shown in Scheme 4. In the first step an aryl halide derivative of formula (10), preferably an aryl bromide or an aryl iodide, is reacted in a Heck-type reaction with an α,β-unsaturated ester compound of formula (11) in the presence of a palladium catalyst such as Pd(OAc)$_2$, a ligand such as triphenylphospine and a base such as triethylamine, according to the procedure described in reference [1]. The reaction is carried out at elevated temperature, preferably at 100° C. The resulting product, an alkene of formula (12) is then hydrogenated using a catalytic amount of palladium on charcoal in the presence of a catalytic amount of zinc bromide according to the procedure of reference [7]. The resulting product, an ester derivative of formula (13), is then reacted with a reagent which is first prepared in situ by treating ethylenediamine with trimethylaluminium at a temperature between 0° C. and room temperature in an inert organic solvent such as toluene, following a procedure reported in references [1], [2] & [8]. The reaction between ester (13) and the aluminium-diakylamine reagent is performed in an inert solvent such as toluene at an elevated temperature such as the reflux temperature of the solvent.

[1] Moormann, A. E. et al. *J. Med. Chem.* 1990, 33, 614-626.
[2] Hlasta, D. J. et al. *J. Med. Chem.* 1987, 30, 1555-1562.
[7] Wu, G. et al. *Synthesis* 2003, 1657-1660.
[8] Gentili, F. et al. *J. Med. Chem.* 2003, 46, 2169-2176.

Alternatively, compounds of formula I in which —CH($R^{3'}$)—CH($R^3$)— can be prepared by methods described in the following references [9]-[11].

[9] Fujioka, H. et al. *Tetrahedron Lett.* 2005, 46, 2197-2199.
[10] Ishihara, M.; Togo, H. *Synlett.* 2006, 227-230.

[11] Melloni, P. et al. *Eur. J. Med. Chem.* 2005, 40, 1206-1213.

Scheme 5 (Method 5)

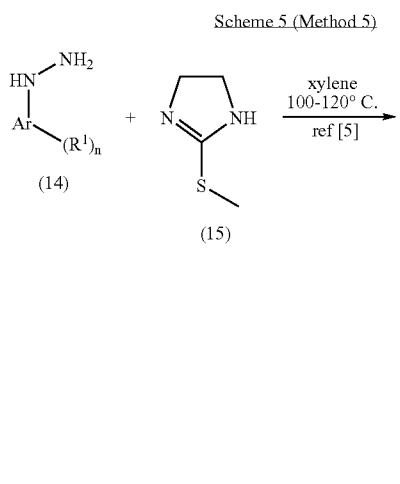

Compounds of formula I in which —X—Y— is —NH—NH— can be prepared by the route shown in Scheme 5. An aryl hydrazine of formula (14) is reacted with 2-methylsulfanyl-4,5-dihydro-1H-imidazole hydrochloride according to the procedure described in reference [6]. The reaction is carried out in an inert solvent such as xylene at elevated temperature, preferably at between 100-120° C.

[12] Stahle, H. et al. U.S. Pat. No. 3,480,630

[13] Behner, O.; Stendel, W.; Andrews, P. DE3133887

Scheme 6 (Method 6)

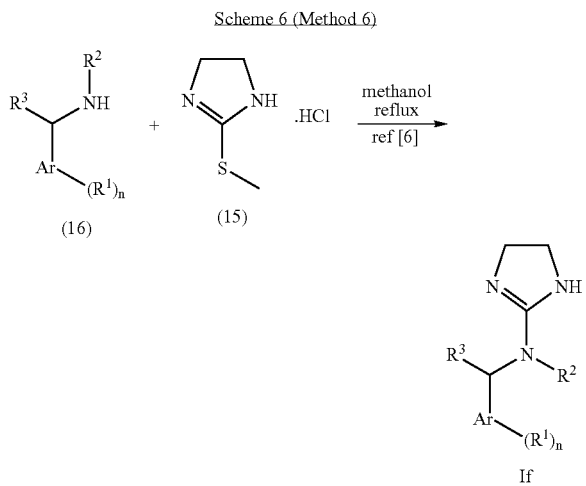

Compounds of formula I in which —X—Y— is —CHR$^3$—N(R$^2$)— can be prepared by the route shown in Scheme 6. An aryl amine of formula (16) is reacted with 2-methylsulfanyl-4,5-dihydro-1H-imidazole hydrochloride according to the procedure described in reference [14]. The reaction is carried out in an alcoholic solvent such as methanol at elevated temperature, preferably at the reflux temperature of the solvent, optionally in the presence of a catalytic amount of a base such as sodium methoxide.

[14] Pinza, M.; LiBassi, G.; Broccali, G.; Pifferi, G. *Heterocycles* 1976, 4, 1699-1706.

Alternative compounds of formula I can be prepared by methods described in the following references [15]-[16].

[15] Kornicka, A.; Saczewski, F.; Gdaniec, M. *Heterocycles* 2006, 68, 687-699.

[16] Kosasayama, A. et al. *Chem. Pharm. Bull.* 1979, 27, 831-840.

Scheme 7 (Method 7)

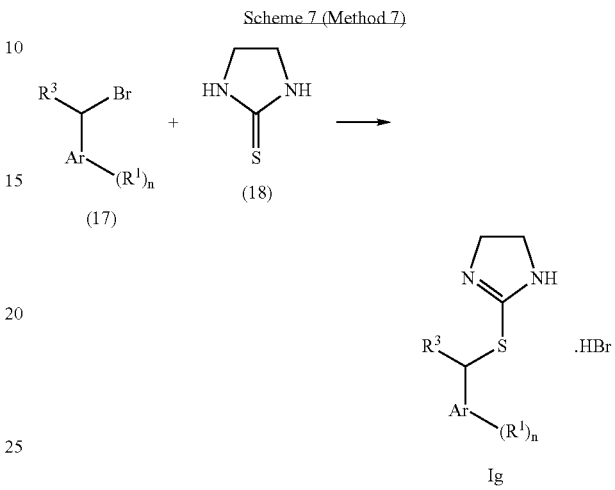

Compounds of formula I in which —X—Y— is —CHR$^3$—S— can be prepared by the route shown in Scheme 7. An arylbromide of formula (17) is reacted with imidazolidine-2-thione according to the procedures described in references [17] & [18]. The reaction is carried out in an alcoholic solvent such as ethanol at elevated temperature, preferably at the reflux temperature of the solvent. The product of formula Ig is obtained as the hydrobromide salt.

[17] Lloyd, D.; Millar, R. W. *Tetrahedron* 1980, 36, 2675-2679.

[18] Chem, J-W.; Rong, J-G. *Tetrahedron Lett.* 1991, 32, 2935-2938.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and can be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM $Mg^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Membrane Preparation and Radioligand Binding

Cells at confluence were rinsed with ice-cold phosphate buffered saline without $Ca^{2+}$ and $Mg^{2+}$ containing 10 mM EDTA and pelleted by centrifugation at 1000 rpm for 5 min at 4° C. The pellet was then washed twice with ice-cold phosphate buffered saline and cell pellet was frozen immediately by immersion in liquid nitrogen and stored until use at −80° C. Cell pellet was then suspended in 20 ml HEPES-NaOH (20 mM), pH 7.4 containing 10 mM EDTA, and homogenized with a Polytron (PT 3000, Kinematica) at 10,000 rpm for 10 s. The homogenate was centrifuged at 48,000×g for 30 min at 4° C. and the pellet resuspended in 20 ml HEPES-NaOH (20 mM), pH 7.4 containing 0.1 mM EDTA (buffer A), and homogenized with a Polytron at 10,000 rpm for 10 s. The homogenate was then centrifuged at 48,000×g for 30 min at 4° C. and the pellet resuspended in 20 ml buffer A, and homogenized with a Polytron at 10,000 rpm for 10 s. Protein concentration was determined by the method of Pierce (Rockford, Ill.). The homogenate was then centrifuged at 48,000×g for 10 min at 4° C., resuspended in HEPES-NaOH (20 mM), pH 7.0 including $MgCl_2$ (10 mM) and $CaCl_2$ g protein per ml and (2 mM) (buffer B) at 200 homogenized with a Polytron at 10,000 rpm for 10 s.

Binding assay was performed at 4° C. in a final volume of 1 ml, and with an incubation time of 30 min. The radioligand [$^3$H]-rac-2-(1,2,3,4-tetrahydro-1-naphthyl)-2-imidazoline was used at a concentration equal to the calculated $K_d$ value of 60 nM to give a bound at around 0.1% of the total added radioligand concentration, and a specific binding which represented approximately 70-80% of the total binding. Non-specific binding was defined as the amount of [$^3$H]-rac-2-(1,2,3,4-tetrahydro-1-naphthyl)-2-imidazoline bound in the presence of the appropriate unlabelled ligand (10 μM). Competing ligands were tested in a wide range of concentrations (10 pM-30 μM). The final dimethylsulphoxide concentration in the assay was 2%, and it did not affect radioligand binding. Each experiment was performed in duplicate. All incubations were terminated by rapid filtration through UniFilter-96 plates (Packard Instrument Company) and glass filter GF/C, pre-soaked for at least 2 h in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 μl/well, Packard Instrument Company) and bound radioactivity was counted by a TopCount Microplate Scintillation Counter (Packard Instrument Company).

The preferred compounds show a $K_i$ value (μM) in mouse on TAAR1<0.1. Representative compounds are shown in the table below.

| Example | $K_i$ (μM) mouse |
|---|---|
| K1 | 0.023 |
| K2 | 0.007 |
| K10 | 0.064 |
| K12 | 0.0063 |
| K17 | 0.0913 |
| K20 | 0.0325 |
| K21 | 0.0262 |
| K25 | 0.0057 |
| 1 | 0.0022 |
| 2 | 0.0011 |
| 3 | 0.0084 |
| 4 | 0.0059 |
| 7 | 0.0028 |
| 8 | 0.0443 |
| 9 | 0.0432 |
| 12 | 0.0158 |
| 13 | 0.025 |
| 14 | 0.0054 |
| 15 | 0.0441 |
| 17 | 0.0372 |
| 20 | 0.0016 |
| 21 | 0.0341 |
| 24 | 0.093 |
| 27 | 0.0329 |
| 31 | 0.0075 |
| 35 | 0.044 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragees, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

The most preferred indications in accordance with the present invention are those, which include disorders of the central nervous system, for example the treatment or prevention of schizophrenia, depression, cognitive impairment and Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

|      |                          | Tablet Formulation (Wet Granulation) mg/tablet | | | |
|------|--------------------------|------|-------|--------|--------|
| Item | Ingredients              | 5 mg | 25 mg | 100 mg | 500 mg |
| 1.   | Compound of formula I    | 5    | 25    | 100    | 500    |
| 2.   | Lactose Anhydrous DTG    | 125  | 105   | 30     | 150    |
| 3.   | Sta-Rx 1500              | 6    | 6     | 6      | 30     |
| 4.   | Microcrystalline Cellulose | 30 | 30    | 30     | 150    |
| 5.   | Magnesium Stearate       | 1    | 1     | 1      | 1      |
|      | Total                    | 167  | 167   | 167    | 831    |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

|      |                      | Capsule Formulation mg/capsule | | | |
|------|----------------------|------|-------|--------|--------|
| Item | Ingredients          | 5 mg | 25 mg | 100 mg | 500 mg |
| 1.   | Compound of formula I | 5   | 25    | 100    | 500    |
| 2.   | Hydrous Lactose      | 159  | 123   | 148    | —      |
| 3.   | Corn Starch          | 25   | 35    | 40     | 70     |
| 4.   | Talc                 | 10   | 15    | 10     | 25     |
| 5.   | Magnesium Stearate   | 1    | 2     | 2      | 5      |
|      | Total                | 200  | 200   | 300    | 600    |

Manufacturing Procedure
1. Mix items 1, 2 and 3 in a suitable mixer for 30 minutes.
2. Add items 4 and 5 and mix for 3 minutes.
3. Fill into a suitable capsule.

EXPERIMENTAL PART

Known Compounds

Example K1

(4-Chloro-phenyl)-(4,5-dihydro-1H-imidazol-2-ylmethyl)-amine

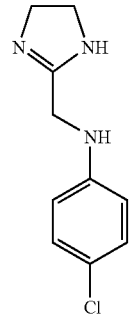

Example K2

(3-Chloro-phenyl)-(4,5-dihydro-1H-imidazol-2-ylmethyl)-amine

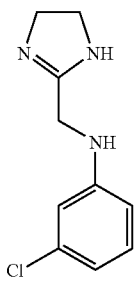

Example K3

(4,5-Dihydro-1H-imidazol-2-ylmethyl)-ethyl-phenyl-amine

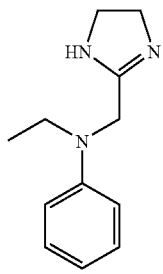

Example K4

3-[(4,5-Dihydro-1H-imidazol-2-ylmethyl)-p-tolyl-amino]-phenol

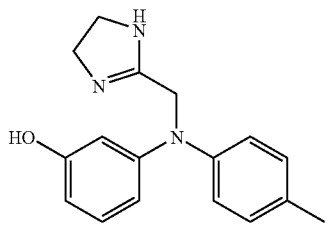

Example K5

Benzyl-(4,5-dihydro-1H-imidazol-2-ylmethyl)-phenyl-amine

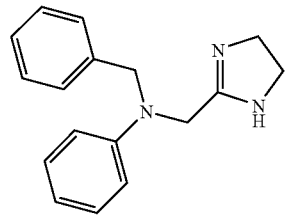

Example K6

2-(4-Benzyl-phenoxymethyl)-4,5-dihydro-1H-imidazole

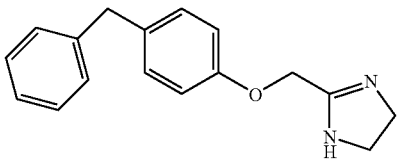

Example K7

2-(4-Phenethyl-phenoxymethyl)-4,5-dihydro-1H-imidazole

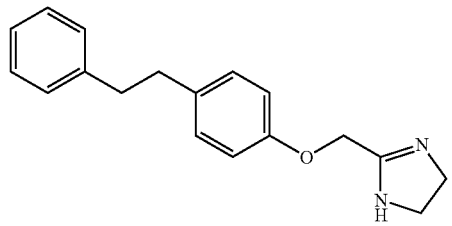

Example K8

2-(2,3,6-Trimethyl-phenoxymethyl)-4,5-dihydro-1H-imidazole

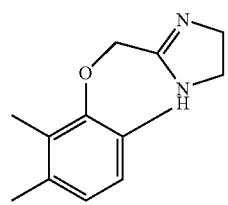

Example K9

2-(2,6-Dichloro-phenoxymethyl)-4,5-dihydro-1H-imidazole

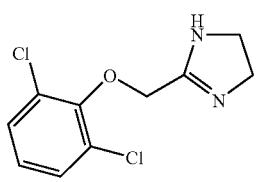

Example K10

2-(2-Chloro-phenoxymethyl)-4,5-dihydro-1H-imidazole

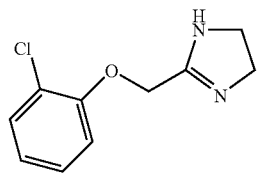

Example K11

2-(Biphenyl-2-yloxymethyl)-4,5-dihydro-1H-imidazole

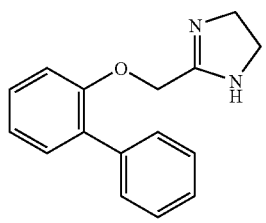

Example K12

2-(2,3-Dichloro-phenoxymethyl)-4,5-dihydro-1H-imidazole

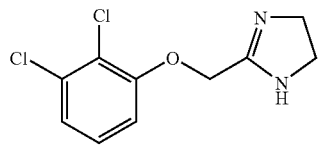

Example K13

2-(Biphenyl-4-yloxymethyl)-4,5-dihydro-1H-imidazole

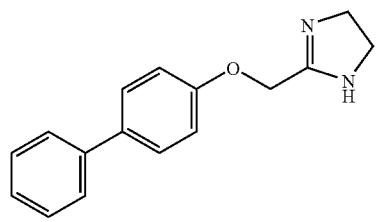

Example K14

2-(2-Methoxy-phenoxymethyl)-4,5-dihydro-1H-imidazole

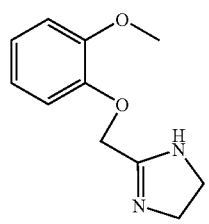

Example K15

2-(Naphthalen-2-yloxymethyl)-4,5-dihydro-1H-imidazole

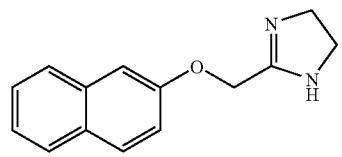

Example K16

2-(4-Chloro-phenoxymethyl)-4,5-dihydro-1H-imidazole

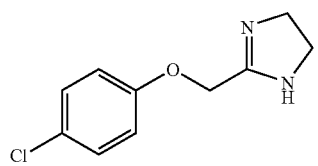

Example K17

2-(3-Trifluoromethyl-phenoxymethyl)-4,5-dihydro-1H-imidazole

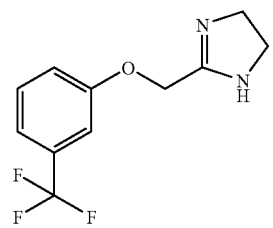

Example K18

2-(2,4-Dichloro-phenoxymethyl)-4,5-dihydro-1H-imidazole

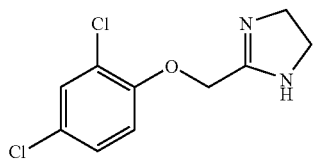

Example K19

2-[1-(2-Benzyloxy-phenoxy)-2-phenyl-ethyl]-4,5-dihydro-1H-imidazole

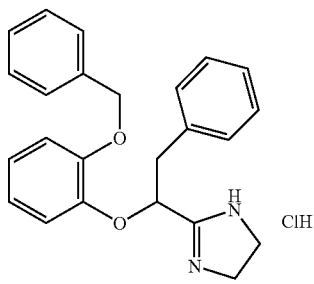

Example K20

2-(2-Cyclopropyl-phenoxymethyl)-4,5-dihydro-1H-imidazole

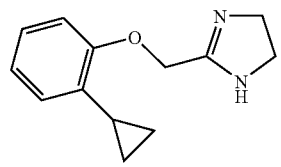

Example K21

2-[1-(2,6-Dichloro-phenoxy)-ethyl]-4,5-dihydro-1H-imidazole

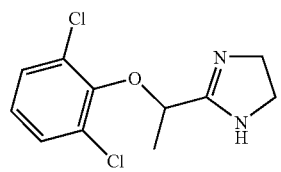

Example K22

2-(3-Chloro-phenoxymethyl)-4,5-dihydro-1H-imidazole

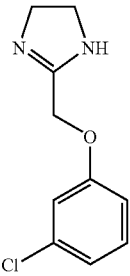

Example K23

2-Phenoxymethyl-4,5-dihydro-1H-imidazole

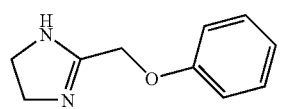

Example K24

2-Phenethyl-4,5-dihydro-1H-imidazole

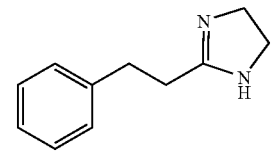

Example K25

N-(3-Chloro-2-methyl-phenyl)-N'-(4,5-dihydro-1H-imidazol-2-yl)-hydrazine

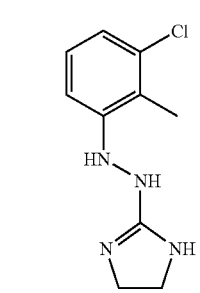

Example K26

Benzyl-(4,5-dihydro-1H-imidazol-2-yl)-amine

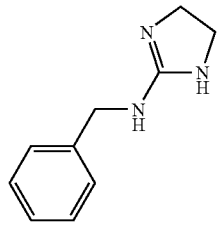

Example K27

2-(3,4-Dichloro-phenylsulfanylmethyl)-4,5-dihydro-1H-imidazole

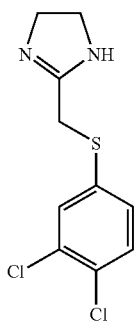

Example K28

2-(2,4-Dichloro-benzylsulfanyl)-4,5-dihydro-1H-imidazole

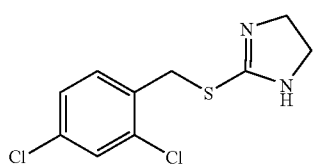

Example K29

2-(3-Chloro-4-propoxy-benzylsulfanyl)-4,5-dihydro-1H-imidazole

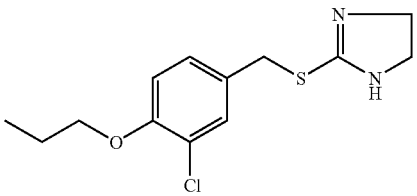

Example K30

2-(3-Nitro-4-propoxy-benzylsulfanyl)-4,5-dihydro-1H-imidazole

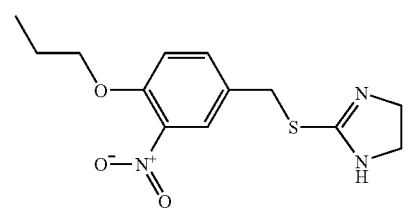

Example K31

2-Benzylsulfanyl-4,5-dihydro-1H-imidazole

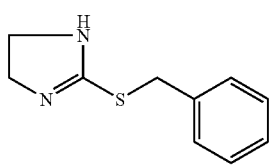

Example K32

2-(2-Chloro-6-fluoro-benzylsulfanyl)-4,5-dihydro-1H-imidazole

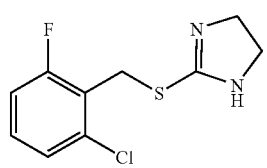

Example K33

2-(3-Chloro-4-ethoxy-benzylsulfanyl)-4,5-dihydro-1H-imidazole

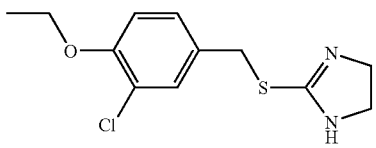

Example K34

2-(2,6-Dichloro-benzylsulfanyl)-4,5-dihydro-1H-imidazole

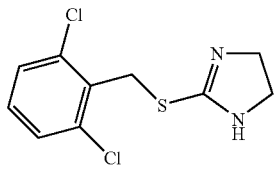

Example K35

2-(3,4-Dichloro-benzylsulfanyl)-4,5-dihydro-1H-imidazole

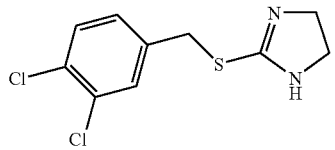

Novel Compounds

Example 1

(4-Bromo-3-chloro-phenyl)-(4,5-dihydro-1H-imidazol-2-ylmethyl)-amine

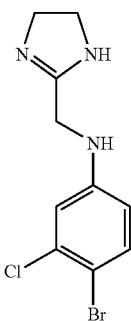

a) (4-Bromo-3-chloro-phenylamino)-acetic acid ethyl ester

To a solution of 4-bromo-3-chloro-aniline (0.64 g, 3.10 mmol) in ethanol (7 ml) were added sodium carbonate (0.49 g, 4.65 mmol) and ethyl bromoacetate (0.38 ml, 3.41 mmol). The resulting suspension was stirred at room temperature for 10 min and was then heated at 100° C. for 30 min under microwave irradiation. The mixture was then cooled to room temperature, diluted with ether, and filtered. The filtrate was washed with 1 M aqueous hydrochloric acid, the phases separated, and the aqueous phase extracted with ether. The combined organic extracts were dried over sodium sulphate, filtered and concentrated in vacuo. The residue was purified by flash chromatography (SiO2: heptane/ethyl acetate=gradient 100:0-70:30) to yield a brown oil (0.56 g, 62%); MS (ISP): 296.1, 294.1, 292.1 ([M+H]$^+$.).

b) (4-Bromo-3-chloro-phenyl)-(4,5-dihydro-1H-imidazol-2-ylmethyl)-amine

To dry toluene (4 ml) under an inert atmosphere at 0° C. was added a toluene solution of trimethylaluminium (1.90 ml, 3.79 mmol, 2 M solution). A solution of ethylenediamine (0.25 ml, 3.79 mmol) in toluene (1.5 ml) was then added dropwise and the reaction mixture was then allowed to warm to room temperature and stirred for 100 min at this temperature before being re-cooled to 0° C. To this mixture was added dropwise a solution of (4-bromo-3-chloro-phenylamino)-acetic acid ethyl ester (0.56 g, 1.90 mmol) in toluene (3 ml). The reaction mixture was then heated at 95° C. for 45 min and then cooled first to room temperature and finally to 0° C. The mixture was quenched by dropwise addition of methanol (1 ml) and when all gas evolution had ceased the mixture was diluted with water and extracted twice with ethyl acetate. The combined organic extracts were dried over sodium sulphate, filtered and concentrated in vacuo. The residue was purified by flash chromatography (SiO2: dichloromethane/methanol=gradient 100:0-98:2) to yield a yellow gum; MS (ISP): 292.1, 290.0, 288.1 ([M+H]$^+$.).

Example 2

(4-Chloro-3-fluoro-phenyl)-(4,5-dihydro-1H-imidazol-2-ylmethyl)-amine

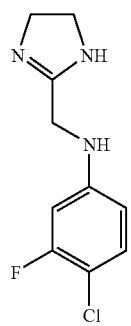

The title compound, MS (ISP): 230.4, 228.1 ([M+H]$^+$.) was obtained in comparable yield analogous to the procedure described for Example 1 using 4-chloro-3-fluoro-aniline instead of 4-bromo-3-chloro-aniline.

Example 3

(3-Chloro-phenyl)-(4,5-dihydro-1H-imidazol-2-ylmethyl)-methyl-amine

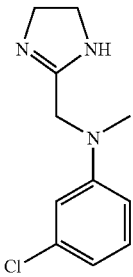

a) [(3-Chloro-phenyl)-methyl-amino]-acetic acid ethyl ester

To a solution of 3-chloro-N-methylaniline (0.50 g, 3.35 mmol) in ethanol (7 ml) were added sodium carbonate (0.53 g, 5.03 mmol) and ethyl bromoacetate (0.42 ml, 3.69 mmol). The resulting suspension was stirred at room temperature for 1 hour and was then heated at 100° C. for 15 min under microwave irradiation. The mixture was then cooled to room temperature, diluted with ether, and filtered. The filtrate was washed with 1 M aqueous hydrochloric acid, the phases separated, and the aqueous phase extracted with ether. The combined organic extracts were dried over sodium sulphate, filtered and concentrated in vacuo. The residue was purified by flash chromatography (SiO2: heptane/ethyl acetate=gradient 100:0-70:30) to yield a brown oil (0.49 g, 64%); MS (ISP): 230.3, 228.1 ([M+H]$^+$.).

b) (3-Chloro-phenyl)-(4,5-dihydro-1H-imidazol-2-ylmethyl)-methyl-amine

To dry toluene (4 ml) under an inert atmosphere at 0° C. was added a toluene solution of trimethylaluminium (2.13 ml, 4.26 mmol, 2 M solution). A solution of ethylenediamine (0.29 ml, 4.26 mmol) in toluene (1.5 ml) was then added dropwise and the reaction mixture was then allowed to warm to room temperature and stirred for 100 min at this temperature before being re-cooled to 0° C. To this mixture was added dropwise a solution of [(3-chloro-phenyl)-methyl-amino]-acetic acid ethyl ester (0.49 g, 2.13 mmol) in toluene (3 ml). The reaction mixture was then heated at reflux for 2.5 h and then cooled first to room temperature and finally to 0° C. The mixture was quenched by dropwise addition of methanol (1 ml) and when all gas evolution had ceased the mixture was diluted with water and extracted twice with ethyl acetate. The combined organic extracts were dried over sodium sulphate, filtered and concentrated in vacuo. The residue was triturated in ether to yield a white solid (0.14 g, 29%) which was collected by filtration; MS (ISP): 226.2, 224.1 ([M+H]$^+$.).

Example 4

(3,4-Dichloro-phenyl)-(4,5-dihydro-1H-imidazol-2-ylmethyl)-methyl-amine

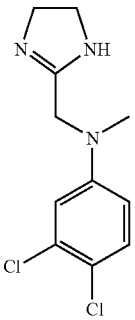

The title compound, MS (ISP): 262.0, 260.0, 258.0 ([M+H]$^+$.) was obtained in comparable yield analogous to the procedure described for Example 3 using 3,4-dichloro-N-methylaniline instead of 3-chloro-N-methylaniline.

Example 5

(4,5-Dihydro-1H-imidazol-2-ylmethyl)-isopropyl-phenyl-amine

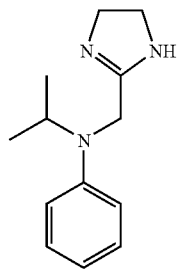

The title compound, MS (ISP): 218.0 ([M+H]$^+$.) was obtained in comparable yield analogous to the procedure described for Example 3 using N-isopropylaniline instead of 3-chloro-N-methylaniline.

Example 6

(4,5-Dihydro-1H-imidazol-2-ylmethyl)-isopropyl-(3-methoxy-phenyl)-amine

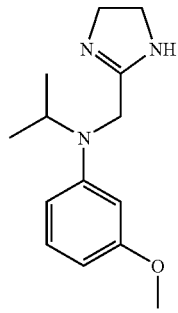

The title compound, MS (ISP): 247.9 ([M+H]$^+$.) was obtained in comparable yield analogous to the procedure described for Example 3 using isopropyl-(3-methoxy-phenyl)-amine instead of 3-chloro-N-methylaniline.

Example 7

(4,5-Dihydro-1H-imidazol-2-ylmethyl)-(4-methyl-benzofuran-5-yl)-amine

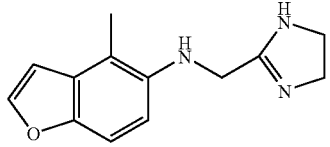

The title compound, MS (ISP): 230.4 ([M+H]⁺.) was obtained in comparable yield analogous to the procedure described for Example 1 using 4-methyl-benzofuran-5-ylamine instead of 4-bromo-3-chloro-aniline.

Example 8

(4,5-Dihydro-1H-imidazol-2-ylmethyl)-[4-(4-methoxy-benzyl)-phenyl]-amine

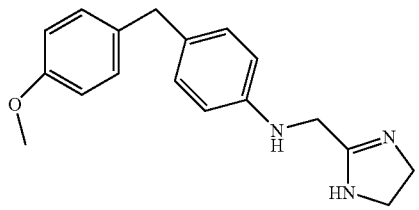

The title compound, MS (ISP): 296.4 ([M+H]⁺.) was obtained in comparable yield analogous to the procedure described for Example 1 using 4-(4-methoxy-benzyl)-phenylamine instead of 4-bromo-3-chloro-aniline.

Example 9

(4,5-Dihydro-1H-imidazol-2-ylmethyl)-(2-methoxy-phenyl)-methyl-amine

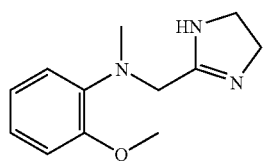

The title compound, MS (ISP): 220.1 ([M+H]⁺.) was obtained in comparable yield analogous to the procedure described for Example 3 using (2-methoxy-phenyl)-methyl-amine instead of 3-chloro-N-methylaniline.

Example 10

2-(4-Chloro-3-fluoro-phenoxymethyl)-4,5-dihydro-1H-imidazole

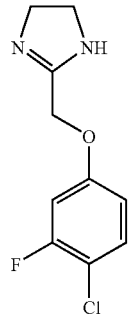

a) (4-Chloro-3-fluoro-phenoxy)-acetic acid ethyl ester

To a solution of 4-chloro-3-fluoro-phenol (0.50 g, 3.34 mmol) in acetonitrile (8 ml) were added caesium carbonate (1.31 g, 4.01 mmol) and ethyl bromoacetate (0.40 ml, 3.51 mmol). The resulting suspension was stirred at room temperature for 1 hour and was then poured onto ice/aq. ammonium chloride solution (50 ml) and the resulting mixture was extracted twice with ethyl acetate. The combined organic extracts were dried over sodium sulphate, filtered and concentrated in vacuo. The residue was purified by flash chromatography (SiO2: heptane/ethyl acetate=gradient 100:0-70:30) to yield a colourless oil (0.81 g, 100%); $^1$H NMR (300 MHz, CDCl3): 7.30 (1H, d), 6.73 (1H, dd), 6.66 (1H, dd), 4.59 (2H, s), 4.28 (2H, q), 1.30 (3H, t).

b) 2-(4-Chloro-3-fluoro-phenoxymethyl)-4,5-dihydro-1H-imidazole

To dry toluene (4 ml) under an inert atmosphere at 0° C. was added a toluene solution of trimethylaluminium (3.44 ml, 6.88 mmol, 2 M solution). A solution of ethylenediamine (0.46 ml, 6.88 mmol) in toluene (1.5 ml) was then added dropwise and the reaction mixture was then allowed to warm to room temperature and stirred for 1 h at this temperature before being re-cooled to 0° C. To this mixture was added dropwise a solution of (4-chloro-3-fluoro-phenoxy)-acetic acid ethyl ester (0.80 g, 3.44 mmol) in toluene (3 ml). The reaction mixture was then heated at 95° C. for 45 min and then cooled first to room temperature and finally to 0° C. The mixture was quenched by dropwise addition of methanol (1 ml) and when all gas evolution had ceased the mixture was diluted with water and extracted twice with ethyl acetate. The combined organic extracts were dried over sodium sulphate, filtered and concentrated in vacuo. The residue was triturated in ether to yield a white solid (0.73 g, 92%) which was collected by filtration; MS (ISP): 231.2, 229.3 ([M+H]⁺.).

Example 11

2-(4-Bromo-3-chloro-phenoxymethyl)-4,5-dihydro-1H-imidazole

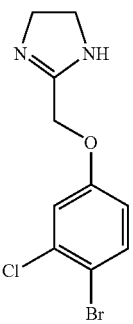

The title compound, MS (ISP): 293.1, 291.0, 289.0 ([M+H]+.) was obtained in comparable yield analogous to the procedure described for Example 10 using 3-chloro-4-bromo-phenol instead of 4-chloro-3-fluoro-phenol.

Example 12

3-{4-[1-(4,5-Dihydro-1H-imidazol-2-yl)-ethoxy]-phenyl}-1-(4-isopropoxy-phenyl)-propan-1-one

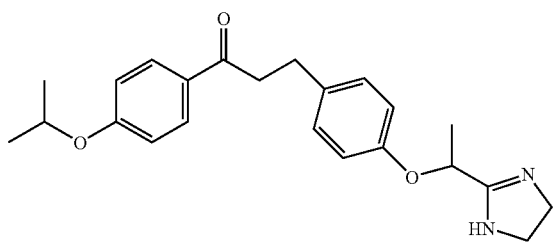

The title compound, MS (ISP): 381.4 ([M+H]+.) was obtained in comparable yield analogous to the procedure described for Example 10 using 3-(4-hydroxy-phenyl)-1-(4-isopropoxy-phenyl)-propan-1-one instead of 4-chloro-3-fluoro-phenol and 2-bromo-propionic acid ethyl ester instead of ethyl bromoacetate.

Example 13

2-[4-(4-Isopropoxy-phenoxymethyl)-phenoxymethyl]-4,5-dihydro-1H-imidazole

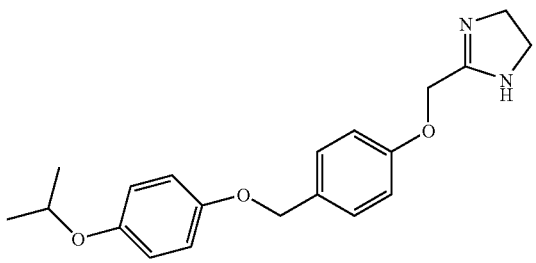

The title compound, MS (ISP): 341.3 ([M+H]+.) was obtained in comparable yield analogous to the procedure described for Example 10 using 4-(4-isopropoxy-phenoxymethyl)-phenol instead of 4-chloro-3-fluoro-phenol.

Example 14

2-(3-Benzyl-phenoxymethyl)-4,5-dihydro-1H-imidazole

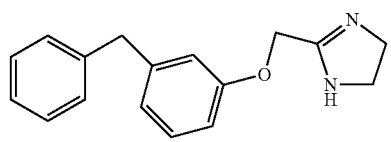

The title compound, MS (ISP): 267.4 ([M+H]+.) was obtained in comparable yield analogous to the procedure described for Example 10 using 3-benzyl-phenol instead of 4-chloro-3-fluoro-phenol.

Example 15

2-[4-(3-Phenyl-propyl)-phenoxymethyl]-4,5-dihydro-1H-imidazole

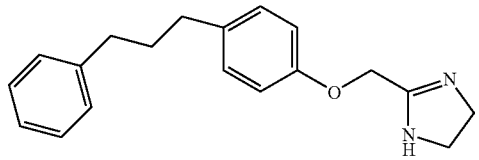

The title compound, MS (ISP): 295.3 ([M+H]+.) was obtained in comparable yield analogous to the procedure described for Example 10 using 4-(3-phenyl-propyl)-phenol instead of 4-chloro-3-fluoro-phenol.

Example 16

6-Bromo-3-(4,5-dihydro-1H-imidazol-2-ylmethoxy)-2-methyl-phenylamine

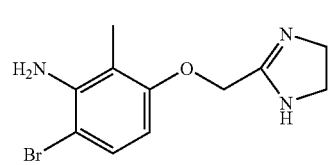

The title compound, MS (ISP): 286.1, 284.3 ([M+H]+.) was obtained in comparable yield analogous to the procedure described for Example 10 using 3-amino-4-bromo-2-methyl-phenol instead of 4-chloro-3-fluoro-phenol.

Example 17

2-(Benzofuran-6-yloxymethyl)-4,5-dihydro-1H-imidazole

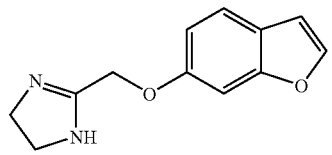

The title compound, MS (ISP): 217.3 ([M+H]$^+$.) was obtained in comparable yield analogous to the procedure described for Example 10 using benzofuran-6-ol instead of 4-chloro-3-fluoro-phenol.

Example 18

2-(4-Bromo-2,6-dimethyl-phenoxymethyl)-4,5-dihydro-1H-imidazole

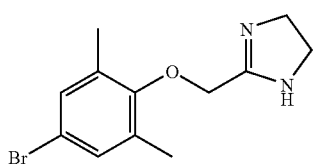

The title compound, MS (ISP): 285.1, 283.2 ([M+H]$^+$.) was obtained in comparable yield analogous to the procedure described for Example 10 using 4-bromo-2,6-dimethyl-phenol instead of 4-chloro-3-fluoro-phenol.

Example 19

2-(2,3-Dimethoxy-phenoxymethyl)-4,5-dihydro-1H-imidazole

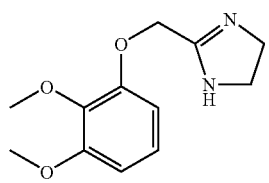

The title compound, MS (ISP): 237.1 ([M+H]$^+$.) was obtained in comparable yield analogous to the procedure described for Example 10 using 2,3-dimethoxy-phenol instead of 4-chloro-3-fluoro-phenol.

Example 20

2-(2-Chloro-3-trifluoromethyl-phenoxymethyl)-4,5-dihydro-1H-imidazole

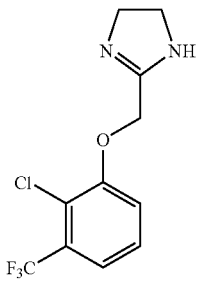

The title compound, MS (ISP): 280.1, 278.1 ([M+H]$^+$.) was obtained in comparable yield analogous to the procedure described for Example 10 using 2-chloro-3-trifluoromethyl-phenol instead of 4-chloro-3-fluoro-phenol.

Example 21

2-(2,3-Difluoro-phenoxymethyl)-4,5-dihydro-1H-imidazole

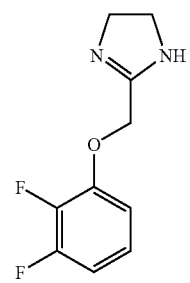

The title compound, MS (ISP): 213.3 ([M+H]$^+$.) was obtained in comparable yield analogous to the procedure described for Example 10 using 2,3-difluoro-phenol instead of 4-chloro-3-fluoro-phenol.

Example 22

2-(2,3,5-Trimethyl-phenoxymethyl)-4,5-dihydro-1H-imidazole

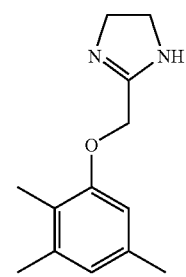

The title compound, MS (ISP): 219.3 ([M+H]$^+$.) was obtained in comparable yield analogous to the procedure described for Example 10 using 2,3,5-trimethyl-phenol instead of 4-chloro-3-fluoro-phenol.

Example 23

2-(2,6-Diethyl-phenoxymethyl)-4,5-dihydro-1H-imidazole

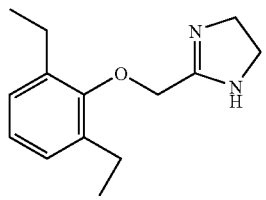

The title compound, MS (ISP): 233.3 ([M+H]$^+$.) was obtained in comparable yield analogous to the procedure described for Example 10 using 2,6-diethyl-phenol instead of 4-chloro-3-fluoro-phenol.

Example 24

4-(4,5-Dihydro-1H-imidazol-2-ylmethoxy)-2,3-dimethyl-phenol

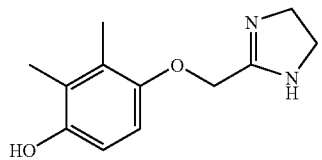

The title compound, MS (ISP): 221.2 ([M+H]$^+$.) was obtained in comparable yield analogous to the procedure described for Example 10 using 2,3-dimethyl-benzene-1,4-diol instead of 4-chloro-3-fluoro-phenol.

Example 25

2-[2-(2,2,2-Trifluoro-ethoxy)-phenoxymethyl]-4,5-dihydro-1H-imidazole

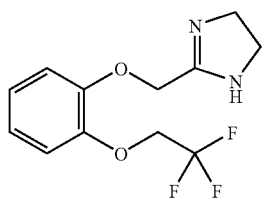

The title compound, MS (ISP): 275.3 ([M+H]-+) was obtained in comparable yield analogous to the procedure described for Example 10 using 2-(2,2,2-trifluoro-ethoxy)-phenol instead of 4-chloro-3-fluoro-phenol.

Example 26

2-[[2-(Phenoxymethyl)phenoxy]methyl]-2-imidazoline

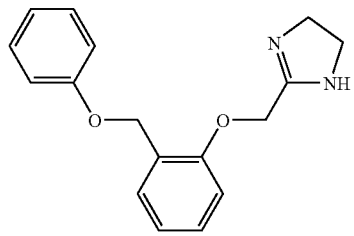

The title compound, MS (ISP): 283.3 ([M+H]$^+$.) was obtained in comparable yield analogous to the procedure described for Example 10 using 2-phenoxymethyl-phenol instead of 4-chloro-3-fluoro-phenol.

Example 27

2-(3,4-Dichloro-phenoxymethyl)-4,5-dihydro-1H-imidazole

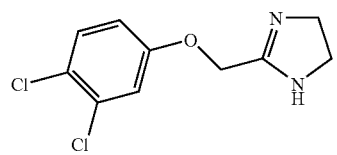

The title compound, MS (ISP): 249.3, 247.3, 245.2 ([M+H]$^+$.) was obtained in comparable yield analogous to the procedure described for Example 10 using 3,4-dichloro-phenol instead of 4-chloro-3-fluoro-phenol.

Example 28

4-(4,5-Dihydro-1H-imidazol-2-ylmethoxy)-phenol

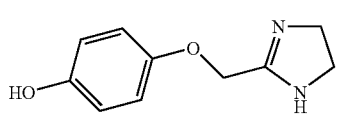

The title compound, MS (ISP): 193.2 ([M+H]$^+$.) was obtained in comparable yield analogous to the procedure described for Example 10 using benzene-1,4-diol instead of 4-chloro-3-fluoro-phenol.

Example 29

2-(3,5-Dichloro-phenylsulfanylmethyl)-4,5-dihydro-1H-imidazole

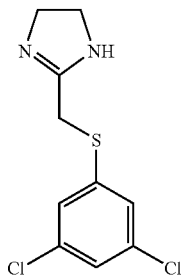

a) (3,5-Dichloro-phenylsulfanyl)-acetic acid ethyl ester

To a solution of 3,5-dichloro-thiophenol (0.50 g, 2.71 mmol) in dichloromethane (8 ml) at 0° C. were added triethylamine (0.49 ml, 3.55 mmol) and a solution of ethyl bromoacetate (0.33 ml, 2.93 mmol) in dichloromethane (2 ml). The resulting solution was stirred at 0° C. for 20 min and then at room temperature for 1 hour. The reaction mixture was then washed sequentially with water and with 1 N aq hydrochloric acid. The organic phase was dried over sodium sulphate, filtered and concentrated in vacuo to yield a light yellow oil (0.72 g, 100%); $^1$H NMR (300 MHz, CDCl3): 7.26 (2H, d), 7.20 (1H, t), 4.21 (2H, q), 3.65 (2H, s), 1.26 (3H, t).

b) 2-(3,5-Dichloro-phenylsulfanylmethyl)-4,5-dihydro-1H-imidazole

To dry toluene (4 ml) under an inert atmosphere at 0° C. was added a toluene solution of trimethylaluminium (2.70 ml, 5.39 mmol, 2 M solution). A solution of ethylenediamine (0.36 ml, 5.39 mmol) in toluene (1.5 ml) was then added dropwise and the reaction mixture was then allowed to warm to room temperature and stirred for 1 h at this temperature before being re-cooled to 0° C. To this mixture was added dropwise a solution of (3,5-dichloro-phenylsulfanyl)-acetic acid ethyl ester (0.72 g, 2.70 mmol) in toluene (3 ml). The reaction mixture was then heated at 95° C. for 45 min and then cooled first to room temperature and finally to 0° C. The mixture was quenched by dropwise addition of methanol (1 ml) and when all gas evolution had ceased the mixture was diluted with water and extracted twice with ethyl acetate. The combined organic extracts were dried over sodium sulphate, filtered and concentrated in vacuo. The residue was triturated in ether to yield a white solid (0.21 g, 30%) which was collected by filtration; MS (ISP): 265.0, 263.1, 261.1 ([M+H]$^+$.).

Example 30

2-(3-Chloro-4-fluoro-phenylsulfanylmethyl)-4,5-dihydro-1H-imidazole

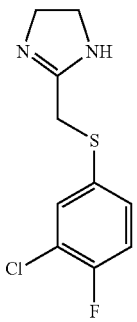

The title compound, MS (ISP): 247.2, 245.2 ([M+H]$^+$.) was obtained in comparable yield analogous to the procedure described for Example 29 using 3-chloro-4-fluoro-thiophenol instead of 3,5-dichloro-thiophenol.

Example 31

2-(2,3-Dichloro-phenylsulfanylmethyl)-4,5-dihydro-1H-imidazole

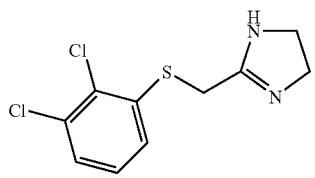

The title compound, MS (ISP): 265.1, 263.1, 261.1 ([M+H]$^+$.) was obtained in comparable yield analogous to the procedure described for Example 29 using 2,3-dichloro-thiophenol instead of 3,5-dichloro-thiophenol.

Example 32

2-(2-Methoxy-phenylsulfanylmethyl)-4,5-dihydro-1H-imidazole

The title compound, MS (ISP): 222.0 ([M+H]$^+$.) was obtained in comparable yield analogous to the procedure described for Example 29 using 2-methoxy-thiophenol instead of 3,5-dichloro-thiophenol.

Example 33

2-[2-(4-Chloro-phenyl)-ethyl]-4,5-dihydro-1H-imidazole

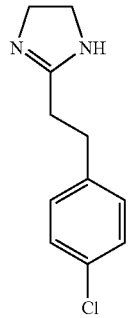

a) (E)-3-(4-Chloro-phenyl)-acrylic acid ethyl ester

To a solution of 1-chloro-4-iodobenezene (0.50 g, 2.08 mmol) in triethylamine (0.93 ml, 6.64 mmol) were added ethyl acrylate (0.36 ml, 3.32 mmol), palladium(II) acetate (5 mg, 0.02 mmol) and triphenylphosphine (11 mg, 0.04 mmol). The mixture was heated in a sealed tube at 100° C. for 1 h and then cooled to room temperature, diluted with ethyl acetate, and washed sequentially with 1 N aq. hydrochloric acid and water. The organic phase was dried over sodium sulphate, filtered and concentrated in vacuo. The residue was purified by flash chromatography (SiO2: heptane/ethyl acetate=gradient 100:0-70:30) to yield a colourless oil (0.37 g, 85%); $^1$H NMR (300 MHz, CDCl3): 7.63 (1H, d), 7.45 (1H, d), 7.36 (1H, d), 6.41 (1H, s), 4.27 (2H, q), 1.34 (3H, t).

b) 3-(4-Chloro-phenyl)-propionic acid ethyl ester

To a solution of (E)-3-(4-chloro-phenyl)-acrylic acid ethyl ester (0.37 g, 1.73 mmol) in ethyl acetate (10 ml) were added palladium on activated charcoal (18 mg) and zinc bromide (80 mg, 0.35 mmol). The reaction vessel was then pressurized with hydrogen gas to a pressure of 1 atmosphere and the mixture was stirred for 18 h. The catalyst was then removed by filtration, washing with ethyl acetate, and the filtrate was concentrated in vacuo to yield a colourless oil which was used for the next step without further purification; MS (ISP): 214.2, 212.1 ([M+H]$^+$.).

c) 2-[2-(4-Chloro-phenyl)-ethyl]-4,5-dihydro-1H-imidazole

To dry toluene (4 ml) under an inert atmosphere at 0° C. was added a toluene solution of trimethylaluminium (2.45 ml, 4.89 mmol, 2 M solution). A solution of ethylenediamine (0.30 ml, 4.89 mmol) in toluene (1.5 ml) was then added dropwise and the reaction mixture was then allowed to warm to room temperature and stirred for 1 h at this temperature before being re-cooled to 0° C. To this mixture was added dropwise a solution of 3-(4-chloro-phenyl)-propionic acid ethyl ester (0.52 g, 2.45 mmol) in toluene (3 ml). The reaction mixture was then heated at 95° C. for 45 min and then cooled first to room temperature and finally to 0° C. The mixture was quenched by dropwise addition of methanol (1 ml) and when all gas evolution had ceased the mixture was diluted with water and extracted twice with ethyl acetate. The combined organic extracts were dried over sodium sulphate, filtered and concentrated in vacuo. The residue was triturated in ether to yield a white solid (0.26 g, 50%) which was collected by filtration; MS (ISP): 211.0, 209.2 ([M+H]$^+$.).

Example 34

N-(3-Chloro-4-methyl-phenyl)-N'-(4,5-dihydro-1H-imidazol-2-yl)-hydrazine

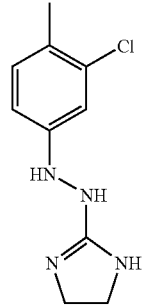

A mixture of 2-methylthio-2-imidazoline hydroiodide (1.83 g, 12 mmol) and 3-chloro-4-methyl-phenylhydrazine (1.87 g, 12 mmol) in xylene (10 ml) was heated to 120° C. overnight. After cooling down to room temperature the precipitate is filtered off and re-crystallised from ethanol, white solid, 0.41 g, MS (ISP): 227.3, 225.3 ([M+H]$^+$.).

Example 35

N-(4,5-Dihydro-1H-imidazol-2-yl)-N'-(3,4-dimethyl-phenyl)-hydrazine

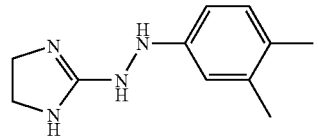

The title compound, MS (ISP): 205.3 ([M+H]$^+$.) was obtained in comparable yield analogous to the procedure described for Example 34 using 3,4-dimethylphenylhydrazine instead of 3-chloro-4-methyl-phenylhydrazine.

Example 36

(3,4-Dichloro-benzyl)-(4,5-dihydro-1H-imidazol-2-yl)-amine hydroiodide

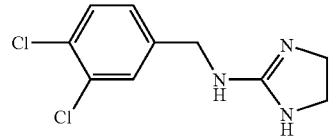

To a solution of 3,4-dichlorobenzylamine (0.352 g, 2.0 mmol) in methanol (5 ml) was added 2-methylthio-2-imidazoline hydroiodide (0.488 g, 2.0 mmol) and the mixture was heated to reflux for 4 h. The solvent was partly removed by evaporation (to approx. 1 ml) and ether (5 ml) was added. After stirring for 15 min the precipitating white solid was removed by filtration and washed with ether. It was obtained 130 mg (18%) of a white solid; MS (ISP): 244.1; 246.0 ([M+H]$^+$.).

Example 37

(4-Chloro-3-fluoro-benzyl)-(4,5-dihydro-1H-imidazol-2-yl)-amine hydroiodide

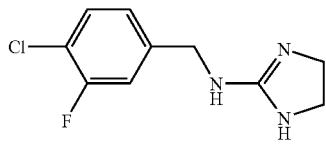

The title compound, MS (ISP): 228.1, 230.1 ([M+H]+.) was obtained in comparable yield analogous to the procedure described for Example 36 using 4-chloro-3-fluoro-benzylamine instead of 3,4-dichloro-benzylamine.

Example 38

(4,5-Dihydro-1H-imidazol-2-yl)-(4-fluoro-naphthalen-1-ylmethyl)-amine hydroiodide

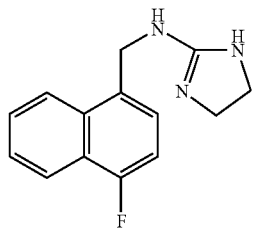

The title compound, MS (ISP): 244.1 ([M+H]+.) was obtained in comparable yield analogous to the procedure described for Example 36 using C-(4-fluoro-naphthalen-1-yl)-methyl amine instead of 3,4-dichloro-benzylamine.

Example 39

Benzo[1,3] dioxol-5-ylmethyl-(4,5-dihydro-1H-imidazol-2-yl)-amine hydroiodide

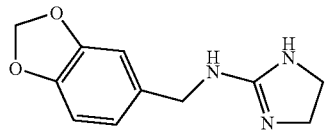

The title compound, MS (ISP): 220.1 ([M+H]+.) was obtained in comparable yield analogous to the procedure described for Example 36 using C-benzo[1,3]dioxol-5-yl-methylamine instead of 3,4-dichloro-benzylamine.

Example 40

2-(4-Chloro-2-fluoro-benzylsulfanyl)-4,5-dihydro-1H-imidazole hydrobromide

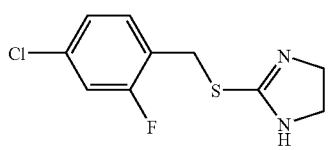

A mixture of 4-chloro-2-fluorobenzylbromide (0.223 g, 1.0 mmol) and N,N'-ethylene thiourea (0.102 g, 1.0 mmol) in acetonitrile (4.5 ml) was heated for 10 min to 110° C. by microwave irradiation. After cooling down to room temperature a solid precipitated that was removed by filtration and washed with ether. It was obtained 260 mg (80%) of a white solid; MS (ISP): 245.0; 247.0 ([M+H]+.).

Example 41

2-(3-Chloro-4-fluoro-benzylsulfanyl)-4,5-dihydro-1H-imidazole hydrobromide

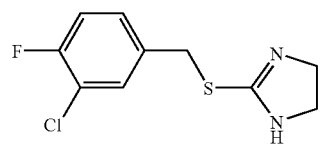

The title compound, MS (ISP): 245.0, 247.1 ([M+H]+.) was obtained in comparable yield analogous to the procedure described for Example 40 using 3-chloro-4-fluoro-benzyl bromide instead of 4-chloro-2-fluoro-benzyl bromide.

Example 42

2-(2-Methyl-benzylsulfanyl)-4,5-dihydro-1H-imidazole hydrobromide

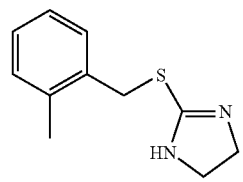

The title compound, MS (ISP): 207.1 ([M+H]+.) was obtained in comparable yield analogous to the procedure described for Example 40 using 2-methyl-benzyl bromide instead of 4-chloro-2-fluoro-benzyl bromide.

Example 43

6-tert-Butyl-3-(4,5-dihydro-1H-imidazol-2-ylsulfanylmethyl)-2,4-dimethyl-phenol

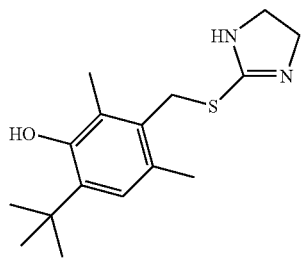

The title compound, MS (ISP): 293.4 ([M+H]+.) was obtained in comparable yield analogous to the procedure described for Example 40 using 3-bromomethyl-6-tert-butyl-2,4-dimethyl-phenol instead of 4-chloro-2-fluoro-benzyl bromide.

The invention claimed is:
1. A compound of formula I

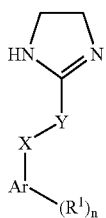

wherein
X—Y is CH(R³)—N(R²)—, —NH—NH—, —O—CHR³—, —CHR³—O—, —S—CHR³, —CHR³—S— or —CHR³—CHR³'—;
R¹ is hydrogen,
halogen,
lower alkyl,
lower alkoxy,
—(CH₂)ₒ-phenyl optionally substituted by lower alkoxy,
—(CH₂)ₒ—C(O)-phenyl optionally substituted by lower alkoxy,
—(CH₂)ₒ—O-phenyl optionally substituted by lower alkoxy,
—(CH₂)ₒ—O-phenyl,
CF₃,
cycloalkyl,
NO₂,
amino or
hydroxy;
R² is hydrogen,
lower alkyl,
phenyl optionally substituted by hydroxy or benzyl;
R³ and R³' are each independently
Hydrogen
or
benzyl;
Ar is phenyl,
naphthyl,
benzofuranyl or
benzo[1,3]dioxolyl;
n is 0, 1, 2, 3 or 4; and
o is 0, 1, 2, 3
or a pharmaceutically active salt thereof, with the exception of the following compounds:
2-(4-benzyl-phenoxymethyl)-4,5-dihydro-1H-imidazole,
2-(4-phenethyl-phenoxymethyl)-4,5-dihydro-1H-imidazole,
2-(2,3,6-trimethyl-phenoxymethyl)-4,5-dihydro-1H-imidazole,
2-(2,6-dichloro-phenoxymethyl)-4,5-dihydro-1H-imidazole,
2-(2-chloro-phenoxymethyl)-4,5-dihydro-1H-imidazole,
2-(biphenyl-2-yloxymethyl)-4,5-dihydro-1H-imidazole,
2-(2,3-dichloro-phenoxymethyl)-4,5-dihydro-1H-imidazole,
2-(biphenyl-4-yloxymethyl)-4,5-dihydro-1H-imidazole,
2-(2-methoxy-phenoxymethyl)-4,5-dihydro-1H-imidazole,
2-(naphthalen-2-yloxymethyl)-4,5-dihydro-1H-imidazole,
2-(4-chloro-phenoxymethyl)-4,5-dihydro-1H-imidazole,
2-(3-trifluoromethyl-phenoxymethyl)-4,5-dihydro-1H-imidazole,
2-(2,4-dichloro-phenoxymethyl)-4,5-dihydro-1H-imidazole,
2-[1-(2-benzyloxy-phenoxy)-2-phenyl-ethyl]-4,5-dihydro-1H-imidazole,
2-(2-cyclopropyl-phenoxymethyl)-4,5-dihydro-1H-imidazole,
2-(3-chloro-phenoxymethyl)-4,5-dihydro-1H-imidazole,
2-phenoxymethyl-4,5-dihydro-1H-imidazole,
2-phenethyl-4,5-dihydro-1H-imidazole,
N-(3-chloro-2-methyl-phenyl)-N'-(4,5-dihydro-1H-imidazol-2-yl)-hydrazine,
benzyl-(4,5-dihydro-1H-imidazol-2-yl)-amine,
2-(3,4-dichloro-phenylsulfanylmethyl)-4,5-dihydro-1H-imidazole,
2-(2,4-dichloro-benzylsulfanyl)-4,5-dihydro-1H-imidazole,
2-(3-chloro-4-propoxy-benzylsulfanyl)-4,5-dihydro-1H-imidazole,
2-(3-nitro-4-propoxy-benzylsulfanyl)-4,5-dihydro-1H-imidazole,
2-benzylsulfanyl-4,5-dihydro-1H-imidazole,
2-(2-chloro-6-fluoro-benzylsulfanyl)-4,5-dihydro-1H-imidazole,
2-(3-chloro-4-ethoxy-benzylsulfanyl)-4,5-dihydro-1H-imidazole,
2-(2,6-dichloro-benzylsulfanyl)-4,5-dihydro-1H-imidazole, and
2-(3,4-dichloro-benzylsulfanyl)-4,5-dihydro-1H-imidazole.

2. A compound of claim 1, wherein Ar is phenyl.
3. A compound of claim 2, wherein X—Y is —O—CHR³—.
4. A compound of claim 3, selected from the group consisting of
2-(2-chloro-phenoxymethyl)-4,5-dihydro-1H-imidazole,
2-(2,3-dichloro-phenoxymethyl)-4,5-dihydro-1H-imidazole,
2-(3-trifluoromethyl-phenoxymethyl)-4,5-dihydro-1H-imidazole,
2-[1-(2,6-dichloro-phenoxy)-ethyl]-4,5-dihydro-1H-imidazole,
2-[4-(4-isopropoxy-phenoxymethyl)-phenoxymethyl]-4,5-dihydro-1H-imidazole,
2-(3-benzyl-phenoxymethyl)-4,5-dihydro-1H-imidazole,
2-[4-(3-phenyl-propyl)-phenoxymethyl]-4,5-dihydro-1H-imidazole,
2-(2-chloro-3-trifluoromethyl-phenoxymethyl)-4,5-dihydro-1H-imidazole,
2-(2,3-difluoro-phenoxymethyl)-4,5-dihydro-1H-imidazole,
4-(4,5-dihydro-1H-imidazol-2-ylmethoxy)-2,3-dimethyl-phenol and
2-(3,4-dichloro-phenoxymethyl)-4,5-dihydro-1H-imidazole.
5. A compound of claim 2, wherein X—Y is —NH—NH—.
6. A compounds of claim 5, selected from the group consisting of N-(3-chloro-2-methyl-phenyl)-N'-(4,5-dihydro-1H-imidazol-2-yl)-hydrazine and N-(4,5-dihydro-1H-imidazol-2-yl)-N'-(3,4-dimethyl-phenyl)-hydrazine.
7. A compound of claim 2, wherein X—Y is —S—CHR³—.
8. A compound of claim 7, which compound is 2-(2,3-dichloro-phenylsulfanylmethyl)-4,5-dihydro-1H-imidazole.
9. A compound of claim 1, wherein Ar is benzofuranyl.
10. A compound of claim 9, wherein X—Y is —N(R²)—CHR³—.

11. A compound of formula I according to claim 10, which compound is (4,5-dihydro-1H-imidazol-2-ylmethyl)-(4-methyl-benzofuran-5-yl)-amine.

12. A compound of claim 9, wherein X—Y is —O—CHR³.

13. A compound of formula I according to claim 12, which compound is 2-(benzofuran-6-yloxymethyl)-4,5-dihydro-1H-imidazole.

14. A compound of claim 1, wherein Ar is naphthyl.

15. A compound of claim 14, wherein X—Y is —CH₂NH.

16. A compound of claim 15, which is (4,5-Dihydro-1H-imidazol-2-yl)-(4-fluoro-naphthalen-1-ylmethyl)-amine hydroiodide.

17. A compound of claim 1, wherein Ar is benzo[1,3]dioxolyl.

18. A compound of claim 17, wherein X—Y is —CH₂NH.

19. A compound of claim 18, which is Benzo[1,3]dioxol-5-ylmethyl-(4,5-dihydro-1H-imidazol-2-yl)-amine hydroiodide.

20. A pharmaceutical composition comprising a therapeutically effective amount of a compound of formula I

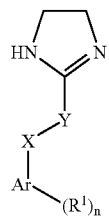

I wherein
X—Y is CH(R³)—N(R²)—, —NH—NH—, —O—CHR³—, —CHR³—O—, —S—CHR³, —CHR³—S— or —CHR³—CHR³'—,
R¹ is hydrogen,
halogen,
lower alkyl,
lower alkoxy,
—(CH₂)$_o$-phenyl optionally substituted by lower alkoxy,
—(CH₂)$_o$—C(O)-phenyl optionally substituted by lower alkoxy,
—(CH₂)$_o$—O-phenyl optionally substituted by lower alkoxy,
—(CH₂)$_o$—O-phenyl,
CF₃,
cycloalkyl,
NO₂,
amino or
hydroxy;
R² is hydrogen,
lower alkyl,
phenyl optionally substituted by hydroxy or
benzyl;
R³ and R³' are each independently
Hydrogen
or
benzyl;

Ar is phenyl,
naphthyl,
benzofuranyl or
benzo[1,3]dioxolyl;
n is 0, 1, 2, 3 or 4; and
o is 0, 1, 2, 3
or a pharmaceutically active salt thereof, with the exception of the following compounds:
2-(4-benzyl-phenoxymethyl)-4,5-dihydro-1H-imidazole,
2-(4-phenethyl-phenoxymethyl)-4,5-dihydro-1H-imidazole,
2-(2,3,6-trimethyl-phenoxymethyl)-4,5-dihydro-1H-imidazole,
2-(2,6-dichloro-phenoxymethyl)-4,5-dihydro-1H-imidazole,
2-(2-chloro-phenoxymethyl)-4,5-dihydro-1H-imidazole,
2-(biphenyl-2-yloxymethyl)-4,5-dihydro-1H-imidazole,
2-(2,3-dichloro-phenoxymethyl)-4,5-dihydro-1H-imidazole,
2-(biphenyl-4-yloxymethyl)-4,5-dihydro-1H-imidazole,
2-(2-methoxy-phenoxymethyl)-4,5-dihydro-1H-imidazole,
2-(naphthalen-2-yloxymethyl)-4,5-dihydro-1H-imidazole,
2-(4-chloro-phenoxymethyl)-4,5-dihydro-1H-imidazole,
2-(3-trifluoromethyl-phenoxymethyl)-4,5-dihydro-1H-imidazole,
2-(2,4-dichloro-phenoxymethyl)-4,5-dihydro-1H-imidazole,
2-[1-(2-benzyloxy-phenoxy)-2-phenyl-ethyl]-4,5-dihydro-1H-imidazole,
2-(2-cyclopropyl-phenoxymethyl)-4,5-dihydro-1H-imidazole,
2-(3-chloro-phenoxymethyl)-4,5-dihydro-1H-imidazole,
2-phenoxymethyl-4,5-dihydro-1H-imidazole,
2-phenethyl-4,5-dihydro-1H-imidazole,
N-(3-chloro-2-methyl-phenyl)-N'-(4,5-dihydro-1H-imidazol-2-yl)-hydrazine,
benzyl-(4,5-dihydro-1H-imidazol-2-yl)-amine,
2-(3,4-dichloro-phenylsulfanylmethyl)-4,5-dihydro-1H-imidazole,
2-(2,4-dichloro-benzylsulfanyl)-4,5-dihydro-1H-imidazole,
2-(3-chloro-4-propoxy-benzylsulfanyl)-4,5-dihydro-1H-imidazole,
2-(3-nitro-4-propoxy-benzylsulfanyl)-4,5-dihydro-1H-imidazole,
2-benzylsulfanyl-4,5-dihydro-1H-imidazole,
2-(2-chloro-6-fluoro-benzylsulfanyl)-4,5-dihydro-1H-imidazole,
2-(3-chloro-4-ethoxy-benzylsulfanyl)-4,5-dihydro-1H-imidazole,
2-(2,6-dichloro-benzylsulfanyl)-4,5-dihydro-1H-imidazole, and
2-(3,4-dichloro-benzylsulfanyl)-4,5-dihydro-1H-imidazole
and a pharmaceutically acceptable carrier.

* * * * *